US007858794B2

(12) United States Patent
Timmers et al.

(10) Patent No.: US 7,858,794 B2
(45) Date of Patent: *Dec. 28, 2010

(54) TETRAHYDROQUINOLINE DERIVATIVES

(75) Inventors: Cornelis Marius Timmers, Oss (NL); Willem Frederik Karstens, Oss (NL)

(73) Assignee: N.V. Organon, Oss (NL)

( * ) Notice: Subject to any disclaimer, the term of this patent is extended or adjusted under 35 U.S.C. 154(b) by 0 days.

This patent is subject to a terminal disclaimer.

(21) Appl. No.: 10/540,336

(22) PCT Filed: Dec. 16, 2003

(86) PCT No.: PCT/EP03/51025

§ 371 (c)(1),
(2), (4) Date: Jan. 10, 2006

(87) PCT Pub. No.: WO2004/056780

PCT Pub. Date: Jul. 8, 2004

(65) Prior Publication Data

US 2006/0142334 A1 Jun. 29, 2006

Related U.S. Application Data

(60) Provisional application No. 60/435,040, filed on Dec. 20, 2002.

(30) Foreign Application Priority Data

Dec. 20, 2002 (EP) .................................. 02102866

(51) Int. Cl.
C07D 215/00 (2006.01)
A61K 31/47 (2006.01)
A61K 31/4709 (2006.01)
(52) U.S. Cl. ..................... 546/165; 514/311; 514/314
(58) Field of Classification Search ................ 546/171, 546/165; 514/311, 314
See application file for complete search history.

(56) References Cited

U.S. PATENT DOCUMENTS

| 2,686,182 | A | 8/1954 | Hopff et al. .................. 260/287 |
| 6,200,963 | B1 | 3/2001 | Wrobel et al. ............... 514/150 |
| 2004/0236109 | A1* | 11/2004 | Van Straten et al. ......... 546/153 |
| 2006/0142334 | A1 | 1/2006 | Timmers |
| 2006/0167047 | A1* | 7/2006 | Timmers et al. ............. 514/313 |

FOREIGN PATENT DOCUMENTS

| EP | 0303 306 B1 | 2/1989 |
| WO | WO 96/19458 | 6/1996 |
| WO | WO 00/08015 | 2/2000 |
| WO | WO 03/004028 A1 * | 1/2003 |

OTHER PUBLICATIONS

The Chemistry of Heterocyclic compounds: Quinolines Part 1, Jones, Gurnos editor Wiley: New York, 1977 p. 104-117.*

Nicole C. R. van Straten et. al. "Identification of Substituted 6-Amino-4-phenyltetrahydroquinoline Derivatives: Potent Antagonists for the Follicle-Stimulating Hormone Receptor" Journal of Medicinal Chemistry 2005, 48, 1697-1700.*
M. Ram Sairam and Hanumanthappa Krishnamurthy "The Role of Follicle-Stimulating Hormone in Spermatogenesis: Lessons from Knockout Animal Models" Archives of Medical Research 32 (2001) 601-608.*
Terry Kenakin and Ongun Onaran "The ligand paradox between affinity and efficacy: can you be there and not make a difference?" TRENDS in Pharmacological Sciences 2002, 23, 275-280.*
Guo, Tao "Small molecule agonists and antagonists for the LH and FSH receptors." Expert Opinion on Therapeutic Patents 2005 15(11) 1555-1564.*
Dorwald F. A. Side Reactions in Organic Synthesis, 2005, Wiley: VCH, Weinheim p. IX of Preface p. 1-15.*
Alfredo Ulloa-Aguirre et. al. "Role of the intracellular domains of the human FSH receptor in G☐S protein coupling and receptor expression." Molecular and Cellular Endocrinology 2007, 260-262, 153-162.*
International Search Report, No. PCT/EP03/51025, Jun. 14, 2004.
Ronald L. Atkins et al., "Substituted Coumarins and Azacoumarins. Synthesis and Fluorescent Properties," J. Org. Chem., vol. 43, No. 10, pp. 1975-1980 (1978).
Jay V. Johnson et al., "2,4-Diamino-5-benzylpyrimidines and Analogues as Antibacterial Agents. 12.1,2-Dihydroquinolymethyl Analogues with High Activity and Specificity for Bacterial Dihydrofolate Reductase," J. Med. Chem. vol. 32, pp. 1942-1949 (1989).
James P. Edwards et al., "5-Aryl-1,2-dihydro-5H-chromeno[3,4-f]quinolines as Potent, Orally Active, Nonsteroidal Progesterone Receptor Agonists: The Effect of D-Ring Substituents," J. Med. Chem. vol. 41, pp. 303-310 (1998).
Lawrence G. Hamann et al., "Synthesis and Biological Activity of a Novel Series of Nonsteroidal, Peripherally Selective Androgen Receptor Antagonists Derived from 1,2-Dihydrophyridono[5,6-g]quinolines," J. Med. Chem, vol. 41, pp. 623-639 (1998).

(Continued)

*Primary Examiner*—Rita J Desai
*Assistant Examiner*—David K O'Dell
(74) *Attorney, Agent, or Firm*—Susan L. Hess; Valerie J. Camara

(57) ABSTRACT

The present invention relates to tetrahydroquinoline derivatives having gene formula (I) or a pharmaceutically acceptable salt thereof, wherein $R^1$ and $R^2$ are H or Me; $R^3$ is H, hydroxy, (1-4C)alkoxy, (di)(1-4C)alkylamino(2-4C)alkoxy or (2-6)heterocycloakl(2-4C)alkoxy; $R^4$ is H, OH, (1-4C) alkoxy or $R^7$; $R^5$ is H, OH, (1-4C)alkoxy or $R^7$, with the proviso that if $R^4$ is H, $R^5$ is not H, OH or (1-4C)alkoxy and that if $R^5$ is H, $R^4$ is not H, OH or (1-4C)alkoxy; $R^6$ is (2-5C) heteroaryl, (6C)aryl, (3-8C)cycloalkyl, (2 6C)heterocycloalkyl or (1-6C)alkyl; $R^7$ is amino, (di)(1-4C)alkylamino, (6C)arylcarbonylamino, (6C)arylcarbonyloxy, (2-5C) heteroarylcarbonylamino, (2-5C)heteroarylcarbonyloxy, $R^8$-(2-4C)alkylamino, $R^8$-(2-4C)alkoxy, $R^9$-methylamino or $R^9$-methoxy; $R^8$ is hydroxy, amino, (-14C)alkoxy, (di)(1-4C) alkylamino, (2-6C)heterocycloalkyl, (2-6C) heterocycloalkylcarbonylamino, (di)(1-4C)alkylaminocarbonylamino, (1-4C)alkoxycarbonylamino and $R^9$ is aminocarbonyl, (di)(1-4C)alkylaminocarbonyl, (2-5C)heteroaryl or (6C)aryl. The present invention also relates to pharmaceutical compositions comprising said derivatives and the use of these derivatives to regulate fertility.

10 Claims, No Drawings

OTHER PUBLICATIONS

Maria-Elena Theoclitou et al, "Novel facile synthesis of 2,2,4 substituted 1,2-dihydroquinolines via a modified Skraup reaction," Tetrahedron Letters 43, pp. 3907-3910 (2002).

Jennifer H. Dorrington et al., "Effects of FSH on Gonadal Functions," Recent Progress in Hormone Research, Vo. 35, pp. 301-342 (1979).

"Gonadotropin Therapy: New Trends and Insights," Int J. Fertil, vol. 33, pp. 85-97 (1988).

Richard M. Sharpe "Intratesticular Control of Steroidogenesis," Clinical Endocrinology, vol. 33, pp. 787-807 (1990).

Jane H. Morse et al., "Heterogeneity of Proteins in Commercial Preparations of Human Chorionic Gonadotropin (hCG) Demonstrated by Western Blotting," American Journal of Reproductive Immunology and Microbiology, vol. 17 pp. 134-140 (1988).

Wiebe Olijive et al., "Molecular biology and biochemistry of human recombinant follicle stimulating hormone (Puregon®)," Molecular Human Reproduction, vol. 2, No. 5, pp. 371-382 (1996).

Daniel Navot et al., "The Use of Follicle-Stimulating Hormone for Controlled Ovarian Hyperstimulation in in Vitro Fertilization," vol. 4, pp. 3-13 (1988).

"Successful in-vitro fertilisation and embryo transfer after treatment with recombinant human FSH," The Lancet, vol. 339, pp. 1170-1171 (1992).

CAS 327981-38-4.
CAS 360760-14-1.
CAS 299418-67-0.
CAS 299970-20-0.

Chemical Abstracts, vol. 79, No. 9, Sep. 3, 1973, Columbux, Ohio, US; abstract No. 53152; Lugovik, B. A. et al: "Structure of compounds obtained from the interaction of 1, 2-dihydroquinolines with alkylbenzenes".

Chemical Abstracts, vol. 77, No. 25, Dec. 18, 1972, Columbus, Ohio, US: abstract No. 164415, Lugovik, B.A.et al: "Reaction of 1, 2-dihydroqunolines with benzene and halobenzenes".

Chemical Abstracts, vol. 105, No. 7, Aug. 18, 1986, Columbus, Ohio, US; abstract No. 56990, Shmyreva, Zh. V. et al: "Modification of anion exchanger Fuolite A 368 PR for the covalent immobilization of glucoamylase".

Chemical Abstracts, "Ambinter Screening Collection", May 31, 2001.

Chemical Abstracts, Columbus Ohio, "VITAS-M Screening Collection", Mar. 22, 2001.

Atanes et. al., "Synthesis of 7-Substituted Dehydronoraporphines, with some Biogenetic Considerations," Tetrahedron 50 (1994) 11257-11266.

Barmettler et. al., "Acid-Catalyzed [3,3]-Sigmatropic Rearrangements of N-Propargylanilines," Helv. Chim. Acta 73 (1990) 1515-1573.

Bonnat et. al., "The Solid Phase Synthesis of a Guanidinium Based 'Tweezer' Receptor," Tetrahedron Lett. 37 (1996) 5409-5412.

Bouyssou et. al., "Synthesis of 7- and 5,7-Substituted-6-fluoro-2-methyl-1,2,3,4-tetrahydroquinolines: Convenient Precursors of Quinolone Antibacterial Agents," J. Heterocycl. Chem. 29 (1992) 895-898.

Cerfontain et al., "The Positional Reactivity Order in the Sulfur Trioxide Sulfonation of Benzene and Naphthalene Derivatives Containing an Electron-Withdrawing Substituent," Recl. Trav. Chim. Pays-Bas, 113 (1994) 403-410.

Coppock, A., "New Synthesis of Aryl Esters of Aromatic Acids," J. Org. Chem. 22 (1957) 325-326.

Edwards et. al., "Lewis-acid Catalyzed Reaction of 2-1sopropenylaniline with Ketones: Improved Synthesis of 2,2,4-Trisubstituted 1,2-Dihydroquinolines," Tetrahedron Lett. 39 (1998) 5139-5142.

Hayler et. al., "The Design and Synthesis of Thrombin Inhibitors: The Introduction of In Vivo Efficacy and Oral Bioavailability into Benzthiazolylalanine Inhibitors," Bioorg. Med. Chem. Lett. 10 (2000) 1567-1570.

Jia et al., "Expression of Human Luteinizing Hormone (LH) Receptor: Interaction with LH and Chorionic Gonadotropin from Human but not Equine, Rat, and Ovine Species," Mol. Endo. 5 (1991) 759-768.

Knoevenagel, E., "Information on the Ketone Anils, I: Preparation of Aliphatic Ketone Anils and Alkaline Hydrolysis of Ketone Anil Iodoalkylates," Ber. Dtsch. Chen. Gesellschaft 54 (1921) 1722-1730 (English-language translation attached.).

Lin et. al., "Substitution Reaction of Tetracyanoethylene with Acetone-Anils," J. Chin. Chem. Soc. 43 (1996) 497-501.

Lugovik et. al., Dokl. Akad. Nauk SSSR, 170:340, 1966 (with English language abstract attached thereto).

Lugovik, B.A., et. al., Khim. Geterosikl. Soedin, 7:795, 1971 (with English language abstract attached thereto).

Lugovik, et al., "Reactions of 1,2-Dihydroxyquinolines IV. Reaction of 2,2,4-Trimethyl-1,2-Dihydroxyquinolines with Cyclohexane," Khimiya geterotsiklicheskikh soedinenii 7 (1972) 977-980, (English-language translation attached.).

Mellor et. al., "Reaction of Electron Rich Alkenes with Anilines and Formaldehyde: Syntheses of Tetrahydroquinolines," Tetrahedron 51 (1995) 6115-6132.

Miyaura et. al., "Palladium-Catalyzed Inter- and Intramolecular Cross-Coupling Reactions of B-Alkyl-9-borabicyclo[3.3.1]none Derivatives with 1-Halo-1-alkenes or Haloarenes," J. Am. Chem. Soc. 111 (1989) 314-321.

Montana et. al., "Aryl Sulfonamides As Selective PDE4 Inhibitors," Bioorg. Med. Chem. Lett. 8 (1998) 2635-2640.

Navot et al., "The Use of Follicle-Stimulating Hormone for Controlled Ovarian Hyperstimulation in in Vitro Fertilization," J. In Vitro Fert. Embryo Transfer 5 (1988) 3-13.

Rao, A.J., "Is there a role for contraceptive vaccines in fertility control?", Journal of Bioscience, vol. 26, No. 4, Suppl., pp. 425-427 (2001).

Schlosser, M., "Selective Mono- or Dimetalation of Arenes by Means of Superbasic Reagents," Tetrahedron 46 (1990) 5633-5648.

Shmyreva et. al., Khim. Tekhnol. 31:45, 1988 (with English language abstract attached thereto).

Shmyreva et. al., Obshch. Khim. 59:1391, 1989 (with English language abstract attached thereto).

Stratowa, et al., "Use of a Luciferase Reporter System for Characterizing G-Protein-Linked Receptors," Curr. Opin. Biotech. 6 (1995) 574-581.

Suzuki, A., "Organoborates in New Synthetic Reactions," Acc. Chem. Res. 15 (1982) 178-184.

Walter, H., "Eine neue einfache Synthese spirocyclischer 1H-Chinolin-Derivate," Helv. Chim. Acta 75 (1992) 1274-1280 (with English language abstract attached thereto).

Walter, H., "A Novel Approach to 2,2-Disubstituted 1,2-Dihydro-4-phenylquinolines," Helv. Chim. Acta 77; (1994) 608-614.

Walter et al., "Acid Catalyzed Reactions of 2-vinylaniline Derivatives with Cyclic Ketones of the Tetralone-, Chroman-4-one- and 2,3-Dihydro-1H-quinolin-4-One Series," Heterocycles 41 (1995) 1251-1269.

International Search Report No. PCT/EP03/51024, Jun. 30, 2004.

Notice of Allowance for U.S. Appl. No. 10/540,335 mail date Aug. 14, 2009.

Non-Final Office Action dated Dec. 5, 2008 for U.S. Appl. No. 10/540,335, filed Jan. 10, 2006.

RN 339273-93-7 Registry.
RN 91147-49-8 Registry.
RN 332904-33-3 Registry.

International Search Report No. PCT/EP02/07053, Oct. 7, 2002.

* cited by examiner

TETRAHYDROQUINOLINE DERIVATIVES

This application claims priority based on International Patent Application No. PCT/ EP2003/051025, filed Dec. 16, 2003, European Patent Application No. 02102866.7, filed Dec. 20, 2002, and US 60/435,040, filed Dec. 20, 2002.

The invention relates to a compound having FSH receptor modulatory activity, in particular a tetrahydroquinoline derivative, to a pharmaceutical composition containing the same, as well as the use of said compound in medical therapy.

Gonadotropins serve important functions in a variety of bodily functions including metabolism, temperature regulation and the reproductive process. Gonadotropins act on specific gonadal cell types to initiate ovarian and testicular differentiation and steroidogenesis. The hypophyseal gonadotropin FSH (follicle stimulating hormone) for example plays a pivotal role in the stimulation of follicle development and maturation whereas LH (luteinizing hormone) induces ovulation (Sharp, R. M. Clin Endocrinol. 33:787-807, 1990; Dorrington and Armstrong, Recent Prog. Horm Res. 35:301-342, 1979). Currently, FSH is applied clinically, in combination with LH or hCG, for ovarian stimulation i.e. ovarian hyperstimulation for in vitro fertilisation (IVF) and induction of ovulation in infertile anovulatory women (Insler, V., Int J. Fertility 33:85-97, 1988, Navot and Rosenwaks, J. Vitro Fert. Embryo Transfer 5:3-13, 1988), as well as for male hypogonadism and male infertility.

The gonadotropin FSH is released from the anterior pituitary under the influence of gonadotropin-releasing hormone and oestrogens, and from the placenta during pregnancy. In the female, FSH acts on the ovaries promoting development of follicles and is the major hormone regulating secretion of oestrogens. In the male, FSH is responsible for the integrity of the seminiferous tubules and acts on Sertoli cells to support gametogenesis. Purified FSH is used clinically to treat infertility in females and for some types of failure of spermatogenesis in males. Gonadotropins destined for therapeutic purposes can be isolated from human urine sources and are of low purity (Morse et al, Amer. J. Reproduct. Immunol. and Microbiology 17:143, 1988). Alternatively, they can be prepared as recombinant gonadotropins. Recombinant human FSH is available commercially and is being used in assisted reproduction (Olijve et at Mol. Hum Reprod. 2:371, 1996; Devroey et al. Lancet 339:1170, 1992).

The actions of the FSH hormone are mediated by a specific plasma membrane receptor that is a member of the Large family of G-protein coupled receptors. These receptors consist of a single polypeptide with seven transmembrane domains and are able to interact with the Gs protein, leading e.g. to the activation of adenylate cyclase.

The FSH receptor is a highly specific target in the ovarian follicle growth process and is exclusively expressed in the ovary. Blocking this receptor or inhibiting the signaling which is normally induced after FSH-mediated receptor activation will disturb follicle development and thus ovulation and fertility. Low molecular weight FSH antagonists could therefore form the basis for new contraceptives. Such FSH antagonists could give rise to diminished follicle development (no ovulation) with still sufficient estrogen production left to avoid adverse effects on e.g. bone mass. On the other hand, compounds that stimulate FSH receptor activity may serve to mimic the gonadotropic effect of the natural ligand.

The present invention describes the preparation of low molecular weight hormone analogs that selectively have modulatory activity on the FSH receptor. The compounds of the invention can either be used as (partial) agonists or (partial) antagonists of the FSH-receptor.

Thus, it has now been found, that the following class of tetrahydroquinoline compounds of formula I or pharmaceutically acceptable salts thereof have FSH-modulatory activity:

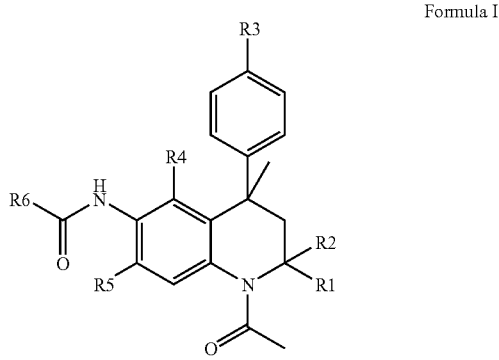

Formula I wherein $R^1$ and $R^2$ are H or Me;

$R^3$ is H, hydroxy, (1-4C)alkoxy, (di)(1-4C)alkylamino(2-4C)alkoxy or (2-6)heterocycloalkyl(2-4C)alkoxy;

$R^4$ is H, OH, (1-4C)alkoxy or $R^7$;

$R^5$ is H, OH, (1-4C)alkoxy or $R^7$;

with the proviso that if $R^4$ is H, $R^5$ is not H, OH or (1-4C)alkoxy and that if $R^5$ is H, $R^4$ is not H, OH or (1-4C)alkoxy;

$R^6$ is (2-5C)heteroaryl, (6C)aryl, (3-8C)cycloalkyl, (2-6C)heterocycloalkyl or (1-6C)alkyl;

$R^7$ is amino, (di)(1-4C)alkylamino, (6C)arylcarbonylamino, (6C)arylcarbonyloxy, (2-5C)heteroarylcarbonylamino, (2-5C)heteroarylcarbonyloxy, $R^8$-(2-4C)alkylamino, $R^8$-(2-4C)alkoxy, $R^9$-methylamino or $R^9$-methoxy;

$R^8$ is hydroxy, amino, (1-4C)alkoxy, (di)(1-4C)alkylamino, (2-6C)heterocycloalkyl, (2-6C)heterocycloalkyl carbonylamino, (di)(1-4C)alkylaminocarbonylamino or (1-4C)alkoxycarbonylamino and $R^9$ is aminocarbonyl (di)(1-4C)alkylaminocarbonyl (2-5C)heteroaryl or (6C)aryl.

$R^4$ and $R^5$ can independently be selected form each of the groups mentioned and need not be the same.

The compounds according to the present invention modulate the FSH receptor function and can be used for the same clinical purposes as native FSH if they behave like agonists, with the advantage that they display altered stability properties and may be administered differently. If they block the FSH receptor they can be used e.g. as a contraceptive agent.

Thus, the FSH-receptor modulators of the present invention may be used for treating infertility, for contraception and for treatment of hormone-dependent disorders such as breast cancer, prostate cancer, and endometriosis.

The following terms are intended to have the indicated meanings denoted below as used in the specification and claims.

The term (1-4C)alkyl as used herein means a branched or unbranched alkyl group to having 1-4 carbon atoms, for example methyl, ethyl propyl, isopropyl, butyl, sec-butyl and tert-butyl.

The term (1-6C)alkyl as used herein means a branched or unbranched alkyl group having 1-6 carbon atoms, for example methyl ethyl, propyl, isopropyl, butyl, sec-butyl tert-butyl and hexyl. (1-5C)Alkyl groups are preferred, (1-4C)alkyl being the most preferred.

The term (3-8C)cycloalkyl means a cycloalkyl group having 3-8 carbon atoms, being cyclopropyl, cyclobutyl, cyclopentyl, cyclohexyl cycloheptyl and cyclooctyl. (3-6C)cycloalkyl groups are preferred.

The term (2-6C)heterocycloalkyl means a heterocycloalkyl group having 2-6 carbon atoms, preferably 3-5 carbon atoms, and at least including one heteroatom selected from N, O and/or S, which may be attached via a heteroatom if feasible, or a carbon atom. Preferred heteroatoms are N or O. Most preferred are piperidinyl piperazinyl, morpholinyl and pyrrolidinyl.

The term (1-4C)alkoxy means an alkoxy group having 1-4 carbon atoms, the alkyl moiety having the same meaning as previously defined. (1-2C)Alkoxy groups are preferred.

The term (2-4C)alkoxy means an alkoxy group having 2-4 carbon atoms, the alkyl moiety having the same meaning as previously defined.

The term (di)(1-4C)alkylamino as used herein means an amino group, monosubstituted or disubstituted with alkyl groups, each of which contain 1-4 carbon atoms and has the same meaning as previously defined.

The term (6C)aryl as used herein means a phenyl group, which may optionally be substituted with one or more substituents selected from hydroxy, amino, iodo, bromo, chloro, fluoro, nitro, trifluoromethyl, cyano, phenyl (1-4C)alkyl, (1-4C)alkoxy, (1-4C)(di)alkylamino, the alkyl, alkoxy and (di)alkylamino moieties having the same meaning as previously defined, for example phenyl, 3,5-dibromophenyl 4-biphenyl, 3,5-dichlorophenyl, 3-bromo-6-methylamino-phenyl, 3-chloro-2,6-dimethoxyphenyl and 3,5-dimethylphenyl.

The term (2-5C)heteroaryl means a substituted or unsubstituted aromatic group having 2-5 carbon atoms, at least including one heteroatom selected from N, O and/or S, like imidazolyl pyridyl, pyrimidyl, thienyl or furyl. The substituents on the heteroaryl group may be selected from the group of substituents listed for the (6C)aryl group. The heteroaryl group may be attached via a carbon atom or a heteroatom, if feasible. Preferred heteroaryl groups are thienyl furyl and pyridyl.

The term di(1-4C)alkylamino(2-4C)alkoxy as used herein means a (di)alkylamino group, the alkyl moiety or alkyl moieties of which each contains 1-4 carbon atoms, connected via the amino group to the alkyl moiety of an alkoxy group having 2-4 carbon atoms, in which the (di)alkylamino group and the alkoxy group have the same meaning as previously defined.

The term (2-6C)heterocycloalkyl(2-4C)alkoxy as used herein means a heterocycloalkyl group having 2-6 carbon atoms, connected to the alkyl moiety of an alkoxy group having 2-4 carbon atoms, in which the alkoxy group and the heterocycloalkyl group have the same meaning as previously defined.

The term (6C)arylcarbonylamino as used herein means a phenyl group, optionally substituted with one or more substituents selected from the group of substituents listed for the (6C)aryl group, connected to the carbonyl moiety of a carbonylamino group, the (6C)aryl moiety having the same meaning as previously defined.

The term (6C)arylcarbonyloxy as used herein means a phenyl group, optionally substituted with one or more substituents selected from the group of substituents listed for the (6C)aryl group, connected to the carbonyl moiety of a carbonyloxy group, the (6C)aryl moiety having the same meaning as previously defined.

The term (2-5C)heteroarylcarbonylamino as used herein means a heteroaryl group containing 2-5 carbon atoms, optionally substituted with one or more substituents selected from the group of substituents listed for the (6C)aryl group, connected to the carbonyl moiety of a carbonylamino group. The heteroaryl moiety in the heteroarylcarbonylamino group has the same meaning as previously defined.

The term (2-5C)heteroarylcarbonyloxy as used herein means a heteroaryl group containing 2-5 carbon atoms, optionally substituted with one or more substituents selected from the group of substituents listed for the (6C)aryl group, connected to the carbonyl moiety of a carbonyloxy group. The heteroaryl moiety in the heteroarylcarbonyloxy group has the same meaning as previously defined.

The term (2-6C)heterocycloalkylcarbonylamino as used herein means a heterocycloalkyl group having 2-6 carbon atoms, connected to the carbonyl moiety of a carbonylamino group, the heterocycloalkyl group having the same meaning as previously defined.

The term (di)(1-4C)alkylaminocarbonyl as used herein means a (di)alkylaminogroup, the alkyl group(s) of which having 14 carbon atoms, connected via the amino group to a carbonyl group, the (di)alkylamino group having the same meaning as previously defined.

The term (di)(1-4C)alkylaminocarbonylamino as used herein means a (di)alkylaminogroup, the alkyl group(s) of which having 1-4 carbon atoms, connected via the amino group to the carbonyl moiety of a carbonylamino group, thus providing a urea functionality, the (di)alkyamino group having the same meaning as previously defined.

The term (1-4C)alkoxycarbonylamino as used herein means an alkoxy group having 1-4 carbon atoms, attached to the carboyl moiety of a carbonylamino group, thus providing a carbamate functionality, the alkoxy group having the same meaning as previously defined.

The term $R^8$-(2-4C)alkylamino as used herein means a $R^8$ group attached to the alkyl moiety of a (2-4C)alkylamino group, having the same meaning as previously defined The term $R^8$-(2-4)alkoxy as used herein means a $R^8$ group attached to the alkyl moiety of a (2-4C) alkoxy group, having the same meaning as previously defined.

The term $R^9$-methylamino as used herein means a $R^9$ group attached to the methyl moiety of a methylamino group.

The term $R^9$-methoxy as used herein means a $R^9$ group attached to the methyl moiety of a methoxy group.

The term pharmaceutically acceptable salt represents those salts which are, within the scope of medical judgement, suitable for use in contact for the tissues of humans and lower animals without undue toxicity, irritation, allergic response and the like, and are commensurate with a reasonable benefit/risk ratio. Pharmaceutically acceptable salts are well known in the art. They may be obtained during the final isolation and purification of the compounds of the invention, or separately by reacting a free base function, if present, with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. If present, an acid function can be reacted with an organic or a mineral base, like sodium hydroxide, potassium hydroxide or lithium hydroxide.

The invention thus relates to the compounds of Formula I as defined here above

In another embodiment the invention relates to compounds according to Formula I, wherein $R^3$ is K hydroxy or (1-4C) alkoxy.

The invention also relates to compounds of formula I, wherein $R^4$ is H, OH or (1-4C)alkoxy.

In another embodiment the invention provides compounds of Formula I wherein $R^5$ is OH, (1-4C)alkoxy or $R^7$.

In another embodiment the invention provides compounds of Formula I wherein $R^6$ is (2-5C)heteroaryl, (6C)aryl, (3-8C)cycloalkyl or (1-6C)alkyl.

In another aspect the invention relates to compounds according to Formula I wherein $R^6$ is (2-5C)heteroaryl or (6C)aryl.

In still another aspect the heteroaryl group in $R^6$ consists of 4 or 5 C atoms.

The invention also relates to compounds according to Formula I wherein $R^7$ is (di)(1-4C)alkylamino, (2-5C)heteroarylcarbonylamino, (2-5C)heteroarylcarbonyloxy, $R^8$-(2-4C)alkoxy, $R^9$-methylamino or $R^9$-methoxy.

Another aspect of the invention are compounds according to Formula I wherein $R^7$ is (di)(1-4C)alkylamino, (2-5C)heteroarylcarbonyloxy, $R^8$-(2-4C)alkoxy, $R^9$-methylamino or $R^9$-methoxy.

In still another aspect the invention relates to compounds according to Formula I wherein $R^7$ is (di)(1-4C)alkylamino, $R^8$-(2-4C)alkoxy, $R^9$-methylamino or $R^9$-methoxy.

In another aspect the invention relates to compounds according to Formula I wherein $R^8$-(2-4C)alkoxy in $R^7$ is $R^8$-ethoxy.

In still another aspect the invention relates to compounds according to Formula I wherein $R^8$-(2-4C)alkylamino in $R^7$ is $R^8$-ethylamino.

In another embodiment the invention provides compounds of Formula I wherein $R^8$ is amino, (di)(1-4C)alkylamino, (2-6C)heterocycloalkyl, (2-6C)heterocycloalkyl carbonylamino or (1-4C)alkoxycarbonylamino.

In another embodiment the invention provides compounds of Formula I wherein $R^8$ is amino, (di)(1-4C)alkylamino, (2-6C)heterocycloalkyl or (1-4C)alkoxycarbonylamino.

In yet another embodiment the invention provides compounds of Formula I wherein $R^8$ is amino, (di)(1-4C)alkylamino, (2-6C)heterocycloalkyl or (2-6C)heterocycloalkyl carbonylamino.

The invention also relates to compounds according to Formula I wherein $R^8$ is amino, (di)(1-4C)alkylamino or (2-6C)heterocycloalkyl.

In yet another aspect of the invention $R^8$ in the compounds of Formula I is (di)(1-4C)alkylamino or (2-6C)heterocycloalkyl.

In another aspect the invention relates to compounds according to Formula I wherein the heterocycloalkyl group in $R^8$ consists of 4 or 5 C atoms.

According to another embodiment of the invention $R^9$ according to Formula I is aminocarbonyl, (2-5C)heteroaryl or (6C)aryl According to yet another embodiment of the invention the heteroaryl group in $R^9$ according to Formula I consists of 3, 4 or 5 C atoms.

Yet another aspect of the invention concerns compounds wherein all specific definitions of the groups $R^1$ through $R^9$ as defined here above are combined in the compound of Formula I.

Suitable methods for the preparation of the compounds of the invention are outlined below.

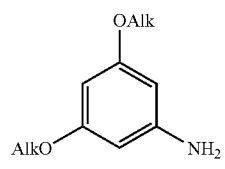

II

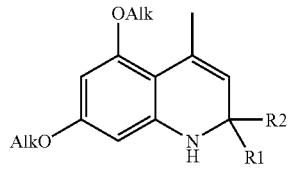

III-a $R^1, R^2$ = Me
III-b $R^1, R^2$ = H

-continued

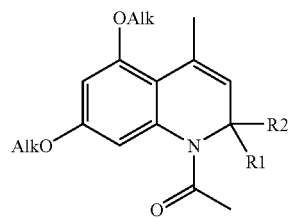

IV-a $R^1, R^2$ = Me
IV-b $R^1, R^2$ = H

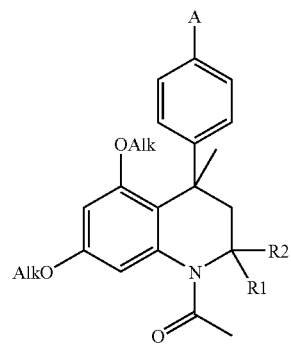

V-a $R^1, R^2$ = Me
V-b $R^1, R^2$ = H

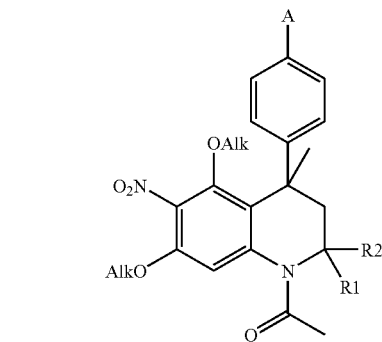

VI-a $R^1, R^2$ = Me
VI-b $R^1, R^2$ = H

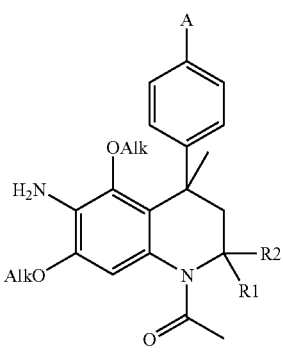

VII-a $R^1, R^2$ = Me
VII-b $R^1, R^2$ = H

-continued

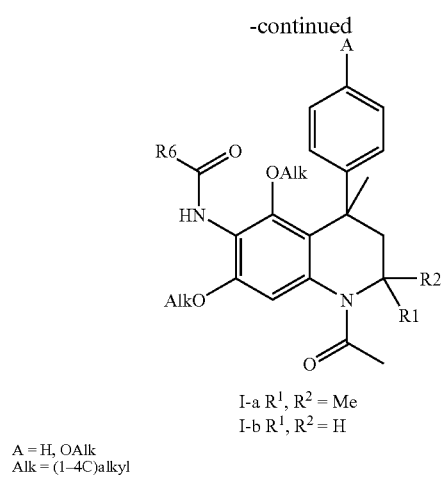

I-a R$^1$, R$^2$ = Me
I-b R$^1$, R$^2$ = H

A = H, OAlk
Alk = (1-4C)alkyl

The compounds of the present invention in which R$^4$ and R$^5$ are (1-4C)alkoxy, R$^1$ and R$^2$ are methyl and R$^6$ is as previously defined can be prepared starting from appropriately substituted anilines of general formula II, by means of the weld documented Skraup reaction, which yields 2,2,4-trimethyl-1,2-dihydroquinoline derivatives of formula III-a.

Related Skraup cyclocondensations are found in literature: A. Knoevenagel, Chem. Ber. 54:1726, 1921; R. L. Atkins and D. E. Bliss, J. Org. Chem. 43:1975, 1978; J. V. Johnson, B. S. Rauckman, D. P. Baccanari and B. Roth, J. Med. Chem. 32:1942, 1989; W. C. Lin, S.-T. Huang and S.-T. Lin, J. Chin. Chem. Soc. 43:497, 1996; J. P. Edwards, S. J. West, K. B. Marschke, D. E. Mais, M. M. Gottardis and T. K. Jones, J. Med. Chem. 41:303, 1998.

The abovementioned reaction is typically conducted at elevated temperature in acetone or mesityl oxide in the presence of iodine or protic acid such as hydrochloric acid, p-toluenesulfonic acid or aqueous hydrogen iodide. Alternatively, 1,2-dihydro-2,2,4-trimethylquinolines of formula II-a can be prepared by reacting the corresponding aniline of formula II with acetone in the presence of MgSO$_4$, 4-tert-butylcatechol and iodine (L. G. Hamann, R. I. Higuchi, L. Zhi, J. P. Edwards and X.-N. Wang, J. Med. Chem, 41:623, 1998). In yet another procedure, the reaction can be performed in acetone using lanthanide triflates (e.g. scandium triflate) as catalysts. In this case, the reaction can be run at room temperature or at elevated temperatures using conventional heating or microwave irradiation (M. E. Theoclitou and L. A. Robinson, Tetrahedron Lett. 43:3907, 2002).

Starting materials can be either obtained directly from commercial sources or easily prepared by those skilled in the art.

Compounds of formula III-b can be prepared from anilines of general formula II by reaction with methyl vinyl ketone. Related cyclizations are described in U.S. Pat. No. 2,686,182 (Badische Anilin- & Soda-Fabrik Aktiengesellschaft).

Subsequent 1-N-acetylation of compounds of formula III-a-b wherein R$^1$, and R$^2$ are as previously defined, can be carried out using standard conditions. In a typical experiment, compounds of formula III are heated under reflux in acetic anhydride or reacted in a solvent such as dichloromethane, tetrahydrofuran, toluene or pyridine with acetyl chloride in the presence of a base such as N,N-diisopropylethylamine, triethylamine or sodium hydride to give N-acetylated 4-methyl-1,2-dihydroquinoline derivatives of formula IV-a-b.

Related N-acylations of a dihydroquinoline scaffold are found in literature: G. Reddelien and A. Thurm, Chem Ber. 65:1511, 1932; Zh. V. Shmyreva, Kh. S. Shikhaliev and E. B. Shpanig, Izv. Vyssh. Uchebn. Zaved., Khim. Khim. Tekhnol. 31:45, 1988; Zh. V. Shmyreva, Kh. S. Shikhaliev, L. P. Zalukaev, Y. A. Ivanov, Y. S. Ryabokobylko and L. E. Pokrovskaya, Zh. Obshch. Khim. 59:1391, 1989.

Introduction of the requisite (substituted) phenyl group at position 4 of the dihydroquinoline scaffold can be accomplished via Friedel-Crafts alkylation of benzene or an appropriately substituted benzene with the compounds of general structure IV-a-b. This reaction is typically conducted at elevated temperatures either in neat benzene or the appropriately substituted benzene or in an appropriate inert solvent such as heptane or hexane with benzene or the appropriately substituted benzene as reagent, under catalysis of a Lewis acid (e.g. AlCl$_3$, AlBr$_3$, FeCl$_3$ or SnCl$_4$). Friedel-Crafts alkylations with 2,2,4-trimethyl-1,2-dihydroquinolines are described in literature by B. A. Lugovik, L. G. Yudin and A. N. Kost, Dokl. Akad. Nauk SSSR, 170:340, 1966; B. A. Lugovik, L. G. Yudin, S. M. Vinogradova and A. N. Kost, Khim Geterosikl. Soedin, 7:795, 1971.

Alternatively, anilines of general structure II can be reacted with an appropriately substituted 1-methylstyrene derivative and formaldehyde in acetonitrile at ambient or elevated temperature to give compounds of general structure V-b. Related cyclizations are described in literature: J. M. Mellor and G. D. Merriman, Tetrahedron, 51:6115, 1995.

Compounds of general structure V-a-b can then be nitrated regioselectively at position 6 of the tetrahydroquinoline scaffold to give compounds of general structure VI-a-b. This reaction is typically conducted at temperatures in the range of –10° C. to room temperature in dichloromethane using a mixture of nitric acid and acetic anhydride as a nitrating reagent. Alternatively, nitric acid can be added to a solution of the compounds of general structure V-a-b in glacial acetic acid or in a mixture of acetic acid and dichloromethane. Related regioselective nitrations of tetrahydroquinolines are described in literature: B. Golankiewicz, Pol. J. Chem., 54:355, 1980; Zh. V. Shmyreva, Kh. S. Shikhaliev, L. P. Zalukaev, Y. A. Ivanov, Y. S. Ryabokobylko and I. E. Pokrovskaya, Zh. Obshch. Khim. 59:1391, 1989.

Reduction of the nitro group of the compounds of general structure VI-a-b can be accomplished by a large variety of methods well known in the art for the reduction of aromatic nitro compounds such as transition metal catalyzed hydrogenation, treatment with sulfides, treatment with iron or other metals and (mild) acid, treatment with tin dichloride under acidic conditions and the like. More specifically, the reduction of the nitro group of the compounds of general formula VI-a-b can be accomplished by treatment with zinc dust and acetic acid in THE or 1,4-dioxane in the temperature range of 0° C. to 100° C.

Subsequent 6-N-acylation of compounds of formula VII-a-b can be carried out using standard conditions, well known to those skilled in the art to give compounds of general structure I-a-b. For example, compounds of formula VII are reacted in a solvent such as dichloromethane, tetrahydrofuran, toluene or pyridine with an acyl halide (R$^6$—C(O)—Cl) or acid anhydride (R$^6$—C(O)—O—C(O)—R$^6$) in the presence of a base

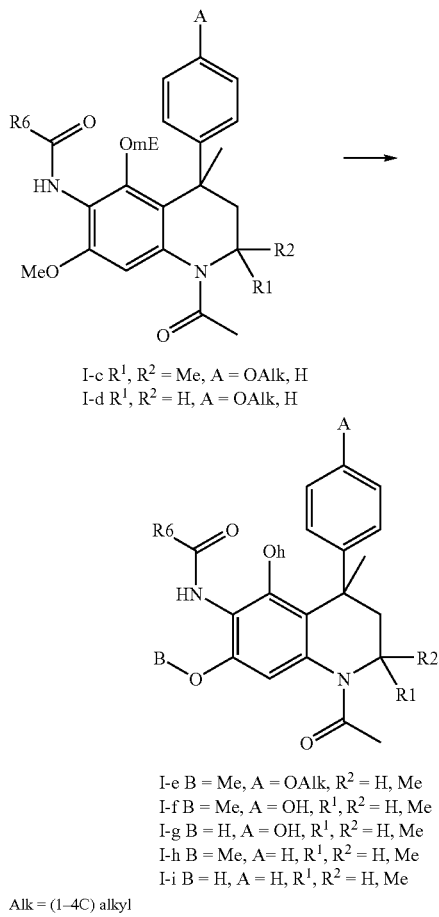

I-c R$^1$, R$^2$ = Me, A = OAlk, H
I-d R$^1$, R$^2$ = H, A = OAlk, H

I-e B = Me, A = OAlk, R$^2$ = H, Me
I-f B = Me, A = OH, R$^1$, R$^2$ = H, Me
I-g B = H, A = OH, R$^1$, R$^2$ = H, Me
I-h B = Me, A= H, R$^1$, R$^2$ = H, Me
I-i B = H, A = H, R$^1$, R$^2$ = H, Me

Alk = (1–4C) alkyl such as N,N-diisopropylethylamine, triethylamine, pyridine or sodium hydride to give 6-N-acylated-1,2,3,4-tetrahydroquinoline derivatives of formula I-a-b. Alternatively, acylation of compounds of general formula VII-a-b to give compounds of general formula I-a-b can also be accomplished by reaction with an appropriate carboxylic acid (R$^6$—CO$_2$H) in the presence of a coupling reagent such as O-benzotriazol-1-yl)-N,N,N',N'-tetramethyluronium tetrafluoroborate (TBTU), O-7-azabenzotriazol-1-yl)-N,N,N',N'-tetramethyluronium hexafluorophosphate (HATU) or bromotripyrrolidinophosphonium hexafluorophosphate (PyBrOP) and a tertiary base, e.g. N,N-diisopropylethylamine, in a solvent such as N,N-dimethylformamide or dichloromethane at ambient or elevated temperature.

Compounds of the present invention wherein R$^3$=H, OH or (1-4C)alkoxy, R$^4$=OH, R$^5$=OH or (1-4C)alkoxy and R$^1$, R$^2$ and R$^6$ are as previously described can be prepared by demethylation reactions of compounds of general formula I-c-d. Demethylation reactions of aromatic methyl ethers are well known to those skilled in the art. In a typical experiment, demethylation is achieved upon reaction of a compound of formula I-c-d with BBr$_3$ in an inert solvent such as dichloromethane at low to ambient temperature to give demethylated compounds of general formula I-e-i. Alternatively, demethylation can be accomplished upon reaction of compounds of formula I-c-d with BF$_3$.Me$_2$S complex at ambient temperature. The degree of demethylation can be controlled to some extent by carefully controlling the reaction temperature and amount of the demethylating reagent. Generally, mixtures of mono-, di- and, if relevant, trihydroxy compounds of general formula I-e-i are obtained, which can be separated by chromatography. The demethylation reaction generally proceeds with a moderate degree of selectivity, with preferential demethylation at position 5 of the tetrahydroquinoline scaffold. The reaction rate for demethylation (dealkylation) of compounds of general formula I-c-d is 5-OMe>4-(p-OAlk-phenyl)>7-OMe.

Compounds of the present invention wherein R$^3$ is H or a (functionalised) alkoxy group and R$^4$ and/or R$^5$ are (functionalised) alkoxy groups or acyloxy groups can be prepared by realkylation or acylation reactions of the hydroxyl groups of compounds of general formula I-e-i with (functionalised) alkyl halides (e.g. chloroethylpyrrolidine) or acyl halides (e.g. 2-furoyl chloride or methyl chloroformate), respectively, under standard conditions.

The compounds of the present invention in which R$^4$=H and R$^5$ is connected to the tetrahydroquinoline scaffold via a nitrogen atom and R$^1$, R$^2$ and R$^6$ are as previously defined can be prepared starting from N-Boc-1,4-phenylene diamine (VIII). The reaction sequence (a) Skraup reaction, (b) acetylation and (c) Friedel-Crafts alkylation of benzene or a substituted benzene as described before leads to the formation of compounds of general formula X-a. It should be noted that the Boc-protective group is cleaved off under the reaction conditions of the Friedel-Crafts reaction.

Alternatively, N-Boc-1,4-phenylene diamine can be treated with methyl vinyl ketone, followed by acetylation and Friedel-Crafts reaction as described before to give compounds of general formula X-b.

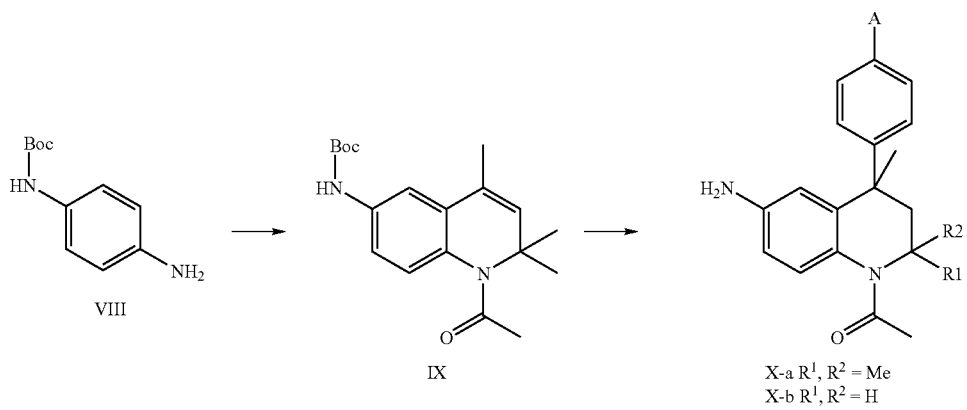

VIII

IX

X-a R$^1$, R$^2$ = Me
X-b R$^1$, R$^2$ = H

-continued

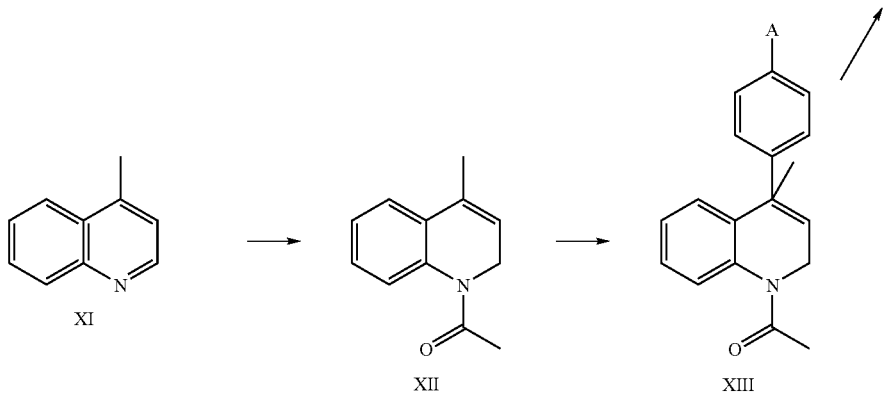

In yet another procedure, compounds of general formula X-b can be obtained staring with the partial reduction of 4-methylquinoline (XI) with $BH_3.THF$ complex and sodium bis(2-methoxy-ethoxy)aluminum dihydride to give 4-methyl-1,2-dihydroquinoline, followed by acetylation as described before to give compound XII. Reductions of related quinolines to 1,2 dihydroquinolines are described in literature: see, for example: D. Roberts and J. A. Joule, J. Org. Chem 62:568, 1997; R. F. Heier, L. A. Dolak, J. N. Duncan, D. K. Hyslop, M. F. Lipton, I. J. Main, M A. Mauragis, M. F. Piercey, N. F. Nichols, P. J. K D. Schreur, M. W. Smith and M. W. Moon, J. Med. Chem 40: 639, 1997. Friedel-Crafts reaction of XII with benzene or an appropriately substituted benzene gives compounds of general formula XIII, which can be converted to compounds of general formula X-b by the regioselective 6-nitration and reduction to the corresponding 6-amino derivative using previously described conditions. Regioselective nitration reactions on similar scaffolds have been reported in literature, see for example: Zh. V. Shmyreva et al., J. Gen. Chem. USSR (Engl. Transl.) 59: 1234, 1989.

Compounds of general formula X-a-b can then be protected with the art known 9-fluorenylmethyloxycarbonyl group (Fmoc-group), see for example: T. W. Greene and P. M. Wuts, Protective groups in organic synthesis (3$^{rd}$ ed., John Wiley & Sons, Inc., 1999, see especially p. 506.). The above-mentioned protection is conveniently carried out using FmocCl in THF with pyridine as a base.

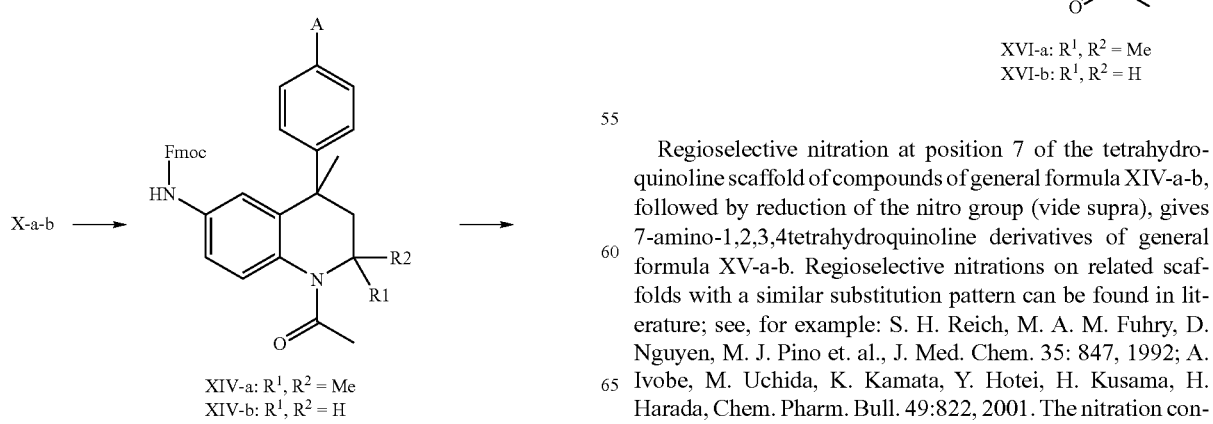

Regioselective nitration at position 7 of the tetrahydroquinoline scaffold of compounds of general formula XIV-a-b, followed by reduction of the nitro group (vide supra), gives 7-amino-1,2,3,4tetrahydroquinoline derivatives of general formula XV-a-b. Regioselective nitrations on related scaffolds with a similar substitution pattern can be found in literature; see, for example: S. H. Reich, M. A. M. Fuhry, D. Nguyen, M. J. Pino et. al., J. Med. Chem. 35: 847, 1992; A. Ivobe, M. Uchida, K. Kamata, Y. Hotei, H. Kusama, H. Harada, Chem. Pharm. Bull. 49:822, 2001. The nitration conditions are similar to those described previously.

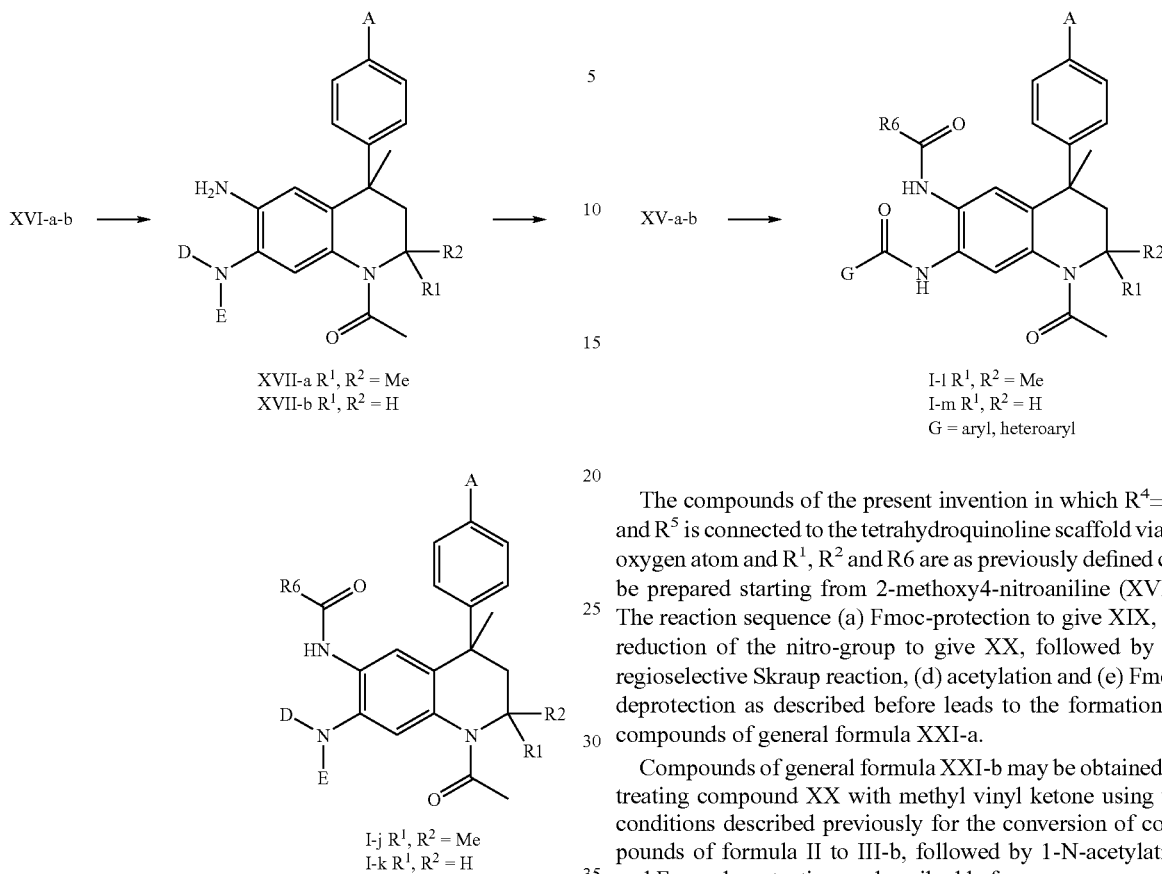

XVII-a R$^1$, R$^2$ = Me
XVII-b R$^1$, R$^2$ = H

I-l R$^1$, R$^2$ = Me
I-m R$^1$, R$^2$ = H
G = aryl, heteroaryl

I-j R$^1$, R$^2$ = Me
I-k R$^1$, R$^2$ = H

Reductive alkylation of the amino group at position 7 of tetrahydroquinoline derivatives of general formula XV-a-b using appropriately substituted aldehydes and a suitable reducing agent (e.g. sodium cyanoborohydride or sodium triacetoxy borohydride) in a suitable solvent such as methanol or N,N-dimethylformamide leads to the formation of compounds of general formula XVIa-b. Generally, formaldehyde leads to the predominant formation of 7-dimethylamino tetrahydroquinoline derivatives (D=E=Me), whereas other aldehydes give rise to the predominant formation of monoalkylated compounds of general formula XVIa-b (D=H, E=(functionalized) alkyl). Reductive alkylations of aromatic amines are well known to those skilled in the art.

Standard cleavage of the Fmoc protective group using piperidine in dichloromethane leads to 6-amino tetrahydroquinoline derivatives of general formula XVII-a-b which can be acylated selectively at position 6 as described before to give compounds of the present invention of general formula I-j-k.

In another procedure, the amino group at position 7 of tetrahydroquinoline derivatives of general formula XV-a-b can be acylated with (hetero)aryl carboxylic acids (G-CO$_2$H) or acyl chlorides (G-C(O)—Cl) as was described previously. In the subsequent steps, the same deprotection-acylation strategy (deprotection of 6-N-Fmoc and acylation of the resulting 6-NH$_2$) that was described previously then leads to compounds of the present invention of general formula I-l-m.

The compounds of the present invention in which R$^4$=H and R$^5$ is connected to the tetrahydroquinoline scaffold via an oxygen atom and R$^1$, R$^2$ and R6 are as previously defined can be prepared starting from 2-methoxy4-nitroaniline (XVII). The reaction sequence (a) Fmoc-protection to give XIX, (b) reduction of the nitro-group to give XX, followed by (c) regioselective Skraup reaction, (d) acetylation and (e) Fmoc-deprotection as described before leads to the formation of compounds of general formula XXI-a.

Compounds of general formula XXI-b may be obtained by treating compound XX with methyl vinyl ketone using the conditions described previously for the conversion of compounds of formula II to III-b, followed by 1-N-acetylation and Fmoc deprotection as described before.

Subsequent conversion of compounds of general formula XXI to XXIII may be effected by acylation of the 6-amino group using an appropriate acylating agent, for example acyl chloride R$^6$—C(O)—Cl, followed by Friedel-Crafts reaction with benzene or an appropriate benzene derivative using conditions described previously. Under the Lewis-acidic conditions of the Friedel-Crafts reaction concomitant demethylation of the 7-OMe function in compounds of general formula XXII occurs. The thus obtained free 7-OH group in compounds of general formula XXIII may be realkylated or acylated with (functionalised) alkyl halides (e.g. chloroethylpyrrolidine) or acyl halides (e.g. 2-furoyl chloride or methyl chloroformate), respectively, under standard conditions to provide compounds of general formula l-n-o (E=functionalized alkyl, acyl or carbamate).

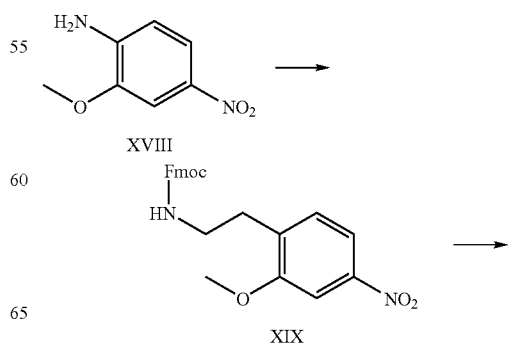

XVIII

XIX

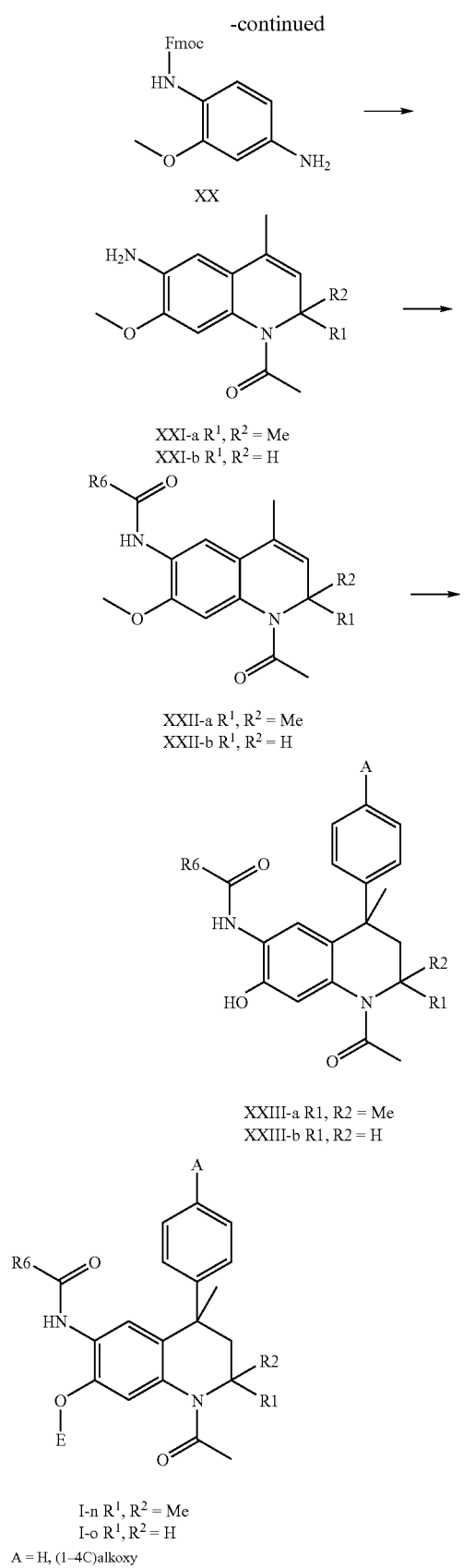

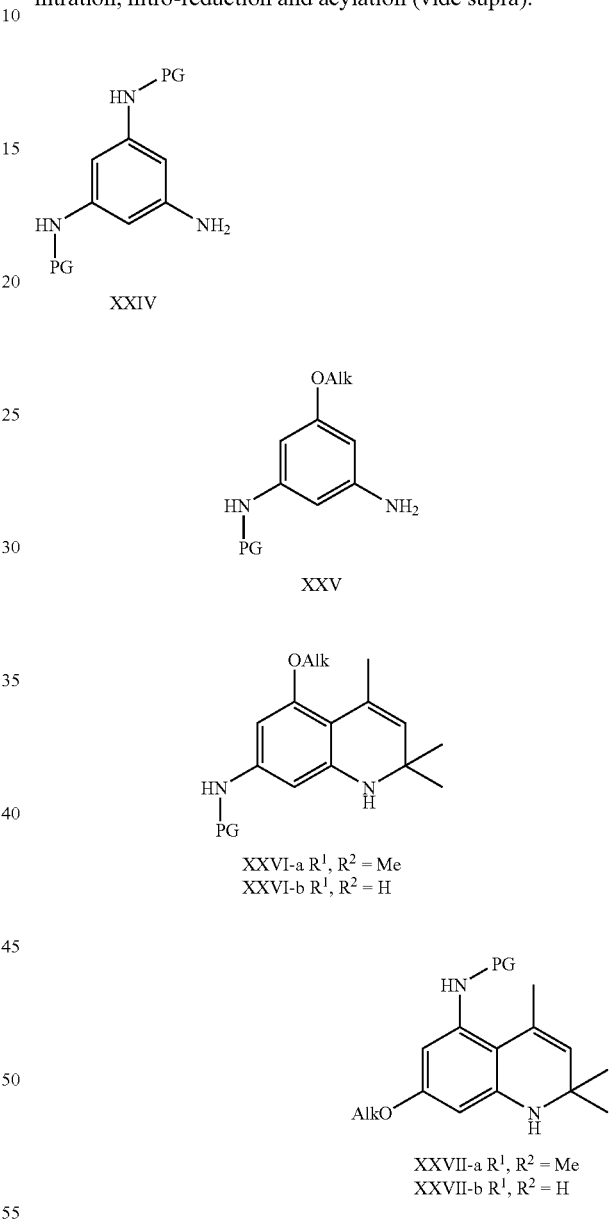

Compounds of the present invention in which $R^4$ and $R^5$ are connected via a nitrogen atom to the tetrahydroquinoline scaffold can be prepared from compounds of general formula XXIV, wherein PG is a nitrogen protective group, e.g. Boc, acetyl, methylcarbamate or Fmoc, via the previously described reactions e.g.: Skraup reaction or cyclocondensation with methyl vinyl ketone, 1-N-acetylation, cleavage of the protective group, N-alkylation, Friedel-Crafts reaction, nitration, nitro-reduction and acylation (vide supra).

Skraup reactions with acetone or mesityl oxide on compounds of general formula XXV may lead to two different regioisomeric products of general formula XXVI-a and XXVII-a, respectively. Conversion of compounds of general formula XXV using methyl vinyl ketone under previously described conditions may afford regioisomeric products with general formula XXVI-b en XXVII-b, respectively. Generally, these regioisomeric dihydroquinolines can be separated using chromatographical techniques (silicagel, HPLC) or crystallization and can subsequently be converted to compounds

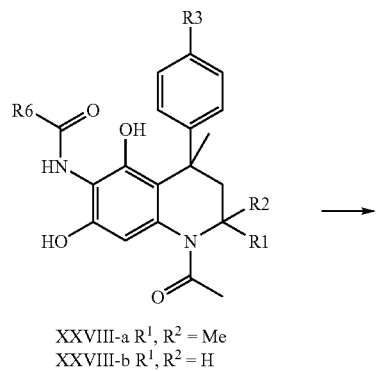 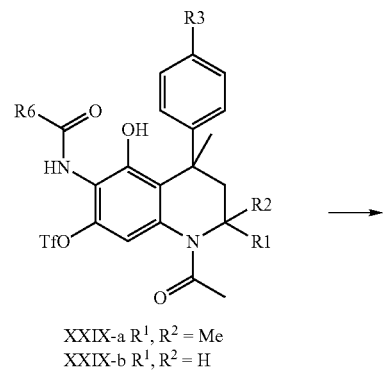 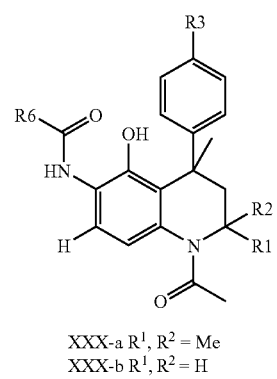

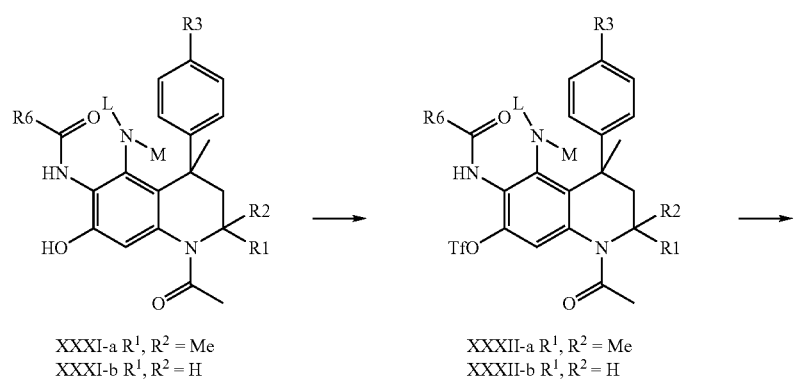 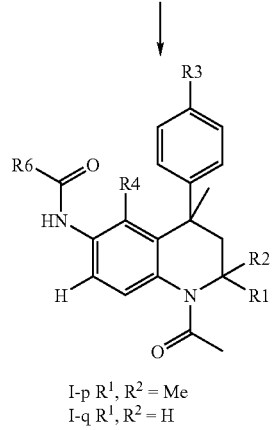

of the current invention via the previously described routes.

Compounds of the present invention wherein $R^5$=H may be prepared by reductive 7-deoxygenation of compounds of general formula XXVIII or XXXI (L and/or M is appropriate (substituted) alkyl, acyl alkyloxycarbonyl or alkylaminocarbonyl) via selective 7-O-triflation and subsequent reduction of the 7-OTf (Tf=trifluoromethylsulfonyl) group. The requisite compounds of general formula XXXI are accessible from derivatives of general formula XXVII using previously described conditions. The (regioselective) triflation reaction may be effected under controlled conditions using $Tf_2N$-phenyl and N,N-diisopropylethyl amine in DMF at room temperature. Generally, preferential triflation of the 7-OH group occurs. The subsequent reduction can be accomplished using a mixture of triphenyl phosphine, trietyl amine, formic acid and palladium(II) acetate as described in the literature. See for example K. A. Parker, Q. Ding, Tetrahedron 56:10249, 2000. Conversion of the thus obtained compounds with general formula XXX or XXXII using previously described conditions then leads to compounds of general formula I-p-q, in which $R^5$=H.

Some of the compounds of the invention, which can be in the form of a free base, may be isolated from the reaction mixture in the form of a pharmaceutically acceptable salt. The pharmaceutically acceptable salts may also be obtained by treating the free base of formula I with an organic or inorganic acid such as hydrogen chloride, hydrogen bromide, hydrogen iodide, sulfuric acid, phosphoric acid, acetic acid, propionic acid, glycolic acid, maleic acid, malonic acid, methanesulphonic acid, fumaric acid, succinic acid, tartaric acid, citric acid, benzoic acid, and ascorbic acid.

The compounds of the present invention possess at least one chiral carbon atom and may therefore be obtained as pure enantiomers, or as a mixture of enantiomers, or as a mixture of diastereomers. Methods for obtaining the pure enantiomers are well known in the art, e.g crystallization of salts which are obtained from optically active acids and the racemic mixture, or chromatography using chiral columns. For diastereomers, straight phase or reversed phase columns may be used.

The compounds of the invention may form hydrates or solvates. It is known to those of skill in the art that charged compounds form hydrated species when lyophilized with water, or form solvated species when concentrated in a solution with an appropriate organic solvent The compounds of this invention include the hydrates or solvates of the compounds listed.

For selecting active compounds testing at $10^{-5}$ M must result in an activity of more than 20% of the maximal activity when FSH is used as a reference. Another criterion might be the $EC_{50}$ value which must be $<10^{-5}$ M, preferably $<10^{-7}$ M.

The skilled artisan will recognize that desirable $EC_{50}$ values are dependent on the compound tested. For example, a compound with an $EC_{50}$ which is less than $10^{-5}$ M is generally considered a candidate for drug selection. Preferably this value is lower than $10^{-7}$ M. However, a compound which has a higher $EC_{50}$, but is selective for the particular receptor, may be even a better candidate.

Methods to determine receptor binding, as well as in vitro and in vivo assays to determine biological activity, of gonadotropins are well known. In general, the expressed receptor is contacted with the compound to be tested and binding or stimulation or inhibition of a functional response is measured.

To measure a functional response, isolated DNA encoding the FSH receptor gene, preferably the human receptor, is expressed in suitable host cells. Such a cell might be the Chinese Hamster Ovary cell but other cells are also suitable. Preferably the cells are of mammalian origin (Jia et al, Mol. Endocrin., 5:759-776, 1991).

Methods to construct recombinant FSH expressing cell lines are well known in the art (Sambrook et al., Molecular Cloning: a Laboratory Manual, Cold Spring Harbor Laboratory Press, Cold Spring Harbor, latest edition). Expression of receptor is attained by expression of the DNA encoding the desired protein. Techniques for site directed mutagenesis, ligation of additional sequences, PCR, and construction of suitable expression systems are all, by now, well known in the art. Portions, or all, of the DNA encoding the desired protein can be constructed synthetically using standard solid phase techniques, preferably to include restriction sites for ease of ligation. Suitable control elements for transcription and translation of the included coding sequence can be provided to the DNA coding sequences. As is well known, expression systems are now available which are compatible with a wide variety of hosts, including prokaryotic hosts such as bacteria and eukaryotic hosts such as yeast, plant cells, insect cells, mammalian cells, avian cells and the like.

Cells expressing the receptor are then contacted with the test compound to observe binding, or stimulation or inhibition of a functional response.

Alternatively, isolated cell membranes containing the expressed receptor may be used to measure binding of compound.

For measurement of binding, radioactively labeled or fluorescently labeled compounds may be used. Also competition binding assays can be performed.

Another assay involves screening for FSH receptor agonist compounds by determining stimulation of receptor mediated cAMP accumulation. Thus, such a method involves expression of the receptor on the cell surface of a host cell and exposing the cell to the test compound. The amount of cAMP is then measured. The level of cAMP can be reduced or increased, depending on the inhibitory or stimulating effect of the test compound upon binding to the receptor.

Screening for FSH receptor antagonists involves incubation of FSH receptor-expressing cells with a concentration range of the test compound in the presence of a fixed, submaximally effective, FSH concentration (i.e., a FSH concentration that induces approximately 80% of the maximal stimulation of cAMP accumulation in the absence of test compound). From the concentration-effect curves, the $IC_{50}$ value and the percentage of inhibition of FSH-induced cAMP accumulation can be determined for each of the test compounds.

In addition to direct measurement of e.g. cAMP levels in the exposed cell, cells lines can be used which in addition to transfection with receptor encoding DNA are also transfected with a second DNA encoding a reporter gene the expression of which responds to the level of cAMP. Such reporter genes might be cAMP inducible or might be constructed in such a way that they are connected to novel cAMP responsive elements. In general, reporter gene expression might be controlled by any response element reacting to changing levels of cAMP. Suitable reporter genes are e.g. the genes encoding β-galactosidase, alkaline phosphatase, firefly luciferase and green fluorescence protein. The principles of such transactivation assays are well known in the art and are described e.g. in Stratowa, Ch., Himmler, A. and Czernilofsky, A. P., (1995) Curr. Opin. Biotechnol. 6:574. As reference compound human recombinant FSH can be used. In the alternative also competition assays can be performed.

The present invention also relates to a pharmaceutical composition comprising a tertrahydroquinoline derivative or pharmaceutically acceptable salts thereof having the general formula I in admixture with pharmaceutically acceptable auxiliaries and optionally other therapeutic agents. The auxiliaries must be "acceptable" in the sense of being compatible with the other ingredients of the composition and not deleterious to the recipients thereof.

Compositions include e.g. those suitable for oral, sublingual subcutaneous, intravenous, intramuscular, local, or rectal administration, and the like, all in unit dosage forms for administration.

For oral administration, the active ingredient may be presented as discrete units, such as tablets, capsules, powders, granulates, solutions, suspensions, and the like.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: *The Science and Practice of Pharmacy* (20th Edition., Lippincott Willams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

The tetrahydroquinoline derivatives of the invention can also be administered in the form of implantable pharmaceutical devices, consisting of a core of active material, encased by a release rate-regulating membrane. Such implants are to be applied subcutaneously or locally, and will release the active ingredient at an approximately constant rate over relatively large periods of time, for instance from weeks to years. Methods for the preparation of implantable pharmaceutical devices as such are known in the art, for example as described in European Patent 0,303,306 (AKZO Nobel N.V.).

The exact dose and regimen of administration of the active ingredient, or a pharmaceutical composition thereof, will necessarily be dependent upon the therapeutic effect to be achieved (treatment of infertility; contraception), and may vary with the particular compound, the route of administration, and the age and condition of the individual subject to whom the medicament is to be administered.

In general parenteral administration requires lower dosages than other methods of administration which are more dependent upon absorption. However, a dosage for humans preferably contains 0.0001-25 mg per kg body weight. The desired dose may be presented as one dose or as multiple subdoses administered at appropriate intervals throughout the day, or, in case of female recipients, as doses to be administered at appropriate daily intervals throughout the menstrual cycle. The dosage as well as the regimen of administration may differ between a female and a male recipient Thus, the compounds according to the invention can be used in therapy.

A further aspect of the invention resides in the use of a tetrahydroquinoline derivative compound having the general formula I for the manufacture of a medicament to be used for the treatment of disorders responsive to FSH receptor mediated pathways. Thus, patients in need thereof can be administered with suitable amounts of the compounds according to the invention.

In another aspect the invention resides in the use of a tetrahydroquinoline derivative compound having the general formula I for the manufacture of a medicament to be used for the control of fertility.

In yet another aspect the invention resides in the use of a tetrahydroquinoline derivative compound having the general formula I for the manufacture of a medicament to be used for the treatment of infertility.

In still another aspect the invention resides in the use of a tetrahydroquinoline derivative compound having the general formula I for the manufacture of a medicament to be used to prevent fertility.

The compounds according to the invention can also be used for the treatment of hormone-dependent disorders such as breast cancer, prostate cancer and endometriosis.

The invention is illustrated by the following examples.

EXAMPLES

General Comments:

The following abbreviations are used in the examples: DMA=N,N-dimethylaniline, DIPEA=N,N-diisopropylethylamine, TEA=trifluoroacetic acid, DtBAD=di-tert-butyl azodicarboxylate, HATU=O-(7-azabenzotriole-1-yl)-N,N, N',N',-tetramethyluronium hexafluorophosphate, Fmoc=9-fluorenylmethoxycarbonyl, Fmoc-Cl=9-fluorenylmethoxycarbonylchloride, DMF=N,N-diimethylformaide, DMAP=4-dimethylaminopyridine, THF=tetrahydrofuran.

Unless stated otherwise, all final products of the examples below are lyophilized from water/1,4-dioxane mixtures or water/acetonitrile mixtures. If the compound was prepared as a HCl- or TFA salt, the respective acids were added in appropriate amounts to the solvent mixture before lyophilization.

The names of the final products described in the examples are generated using the Beilstein Autonom program (version: 2.02.119).

The following analytical HPLC methods are used for determination of retention times:

Method 1: Column: 5 μm Luna C-18(2) 150×4.6 mm; flow: 1 ml/min; detection: 210 nm; column temperature: 40° C.; solvent A: $CH_3CN/H_2O=1/9$ (v/v); solvent B: $CH_3CN$; solvent C: 0.1 M aqueous trifluoroacetic acid; gradient: solvent A/B/C=65/30/5 to 10/85/5 (v/v/v) in 30.00 min, then constant for an additional 10.00 min at A/B/C=10/85/5 (v/v/v).

Method 2: Identical to method 1, except for the gradient used: Gradient: solvent A/B/C=75/20/5 to 15/80/5 (v/v/v) in 30.00 min, then constant for an additional 10.00 min at A/B/C=15/80/5 (v/v/v).

Method 3: Identical to method 1, except for the gradient used: Gradient solvent A/B/C=35/60/5 to 10/85/5 (v/v/v) in 30.00 min, then constant for an additional 10.00 min at A/B/C=10/85/5 (v/v/v).

Method 4: Column: 3 μm Luna C-18(2) 100×2 mm; flow: 0.25 ml/min; detection: 210 nm; column temperature: 40° C.; solvent A: $H_2O$; solvent B: $CH_3CN$; gradient: solvent A/B=75/25 to 0/100 (v/v) in 20.00 min, then constant for an additional 10.00 min at A/B=0/100 (v/v).

Method 5: Column: 3 μm Luna C-18(2) 100×2 mm; flow: 0.25 ml/min; detection: 210 nm; column temperature: 40° C.; solvent A: $H_2O$; solvent B: $CH_3CN$; solvent C: 50 mM phosphate buffer, pH 2.1; gradient: solvent A/B/C=70/20/10 to 10/80/10 (v/v/v) in 20.00 min, then constant for an additional 10.00 min at A/B/C=10/80/10 (v/v/v).

Method 6: Identical to method 5, except for the gradient used: Gradient: solvent A/B/C=65/30/5 to 10/85/5 (v/v/v) in 20.00 min, then constant for an additional 10.00 min at A/B/C=10/85/5 (v/v/v).

The following methods are used for preparative HPLC-purifications:

Method A: Column=Luna C-18. Gradient: 0.1% trifluoroacetic acid in $H_2O/CH_3CN$ (9/1, v/v)/$CH_3CN$=80/20 to 0/100 (v/v) in 30-45 min, depending on the ease of separation. Detection: 210 nm.

Method B: Column=Luna C-18. Gradient-$H_2O/CH_3CN$ (9/1, v/v)/$CH_3CN$=80/20 to 0/100 (v/v) in 30-45 min, depending on the ease of separation. Detection: 210 nm.

Example 1

N-[1-Acetyl-5,7-dimethoxy-4-(4-methoxy-phenyl)-2,2,4-trimethyl-1,2,3,4-tetrahydro-quinolin-6-yl]-3-chloro-2,6-dimethoxy-benzamide (a). 5,7-Dimethoxy-2,2,4-trimethyl-1,2-dihydroquinoline A solution of 3,5-dimethoxyaniline (50 g) in acetone (800 ml) was added dropwise to a mixture of $MgSO_4$ (100 g) and $Sc(OTf)_3$ (8.0 g) in 1 l of acetone at room temperature. After 5 h another portion of $Sc(OTf)_3$ (3.2 g) was added and the reaction mixture was stirred until no staring material remained. After filtration, the acetone was partially evaporated in vacuo causing crystallization of the title compound which was collected by filtration to yield 22 g after drying in vacuo. The remaining mother liquor was concentrated in vacuo and the residue was purified by chromatography on silicagel using heptane/ethyl acetate=1/0=>0/1 (v/v) as the eluent to give an additional 19.4 g of the title compound.

Yield: 42 g.

(b). Acetyl-5,7-dimethoxy-2,2,4-trimethyl-1,2-dihydroquinoline

A mixture of the compound described in example 1a (42 g) and acetic anhydride (100 ml) was stirred at 100° C. for 20 h. The reaction mixture was poured in 500 ml of ice-water while stirring. The precipitated solids were collected by filtration and dried in vacuo at 40° C. for 2 days. The remaining brown solid could be used crude for further synthetic transformations.

Yield: 45 g.

(c) 1-Acetyl-5,7-dimethoxy-4-(4-methoxyphenyl)-2,2,4-trimethyl-1,2,3,4-tetrahydroquinoline A mixture of the compound described in example 1b (30 g) and AlCl$_3$ (44 g) in anisole (500 ml) was stirred at 50° C. for 18 h. The reaction mixture was cooled (0° C.) and quenched with water and ethyl acetate was added. The mixture was stirred overnight. The organic layer was separated, dried over MgSO$_4$, filtered and concentrated in vacuo. The residue was chromatographed on silicagel using heptane/ethyl acetate=8/2 (v/v) as the eluent.
Yield: 15 g.

(d). 1-Acetyl-5,7-dimethoxy-4-(4-methoxyphenyl)-2,2,4-trimethyl-6-nitro-1,2,3,4-tetrahydroquinoline A solution of acetic anhydride (450 µl) in fuming nitric acid (22.5 ml) was added dropwise to a solution of the compound described in example 1c (15 g) in CH$_2$Cl$_2$ (500 ml) at 0° C. After complete addition the reaction mixture was stirred at room temperature for 3 h. Water was added and the organic layer was separated, dried over MgSO$_4$, filtered and concentrated in vacuo. The residue was crystallized from ethanol to give the tie compound as a crystalline solid.
Yield: 10 g.

(e). 1-Acetyl-6-amino-5,7-dimethoxy-4-(4-methoxyphenyl)-2,2,4-trimethyl-1,2,3,4-tetrahydroquinoline A solution of the compound described in example 1d (11.75 g) and acetic acid (15.5 ml) in THF (600 ml) was cooled to 0° C. Zinc dust (36 g) was added in portions and the ice-bath removed. The temperature rose rapidly to 30° C., after which the reaction mixture was allowed to cool down to room temperature. The excess of zinc was removed by filtration and to the filtrate was added CH$_2$Cl$_2$ and a saturated aqueous solution of Na$_2$CO$_3$. The organic layer was separated dried over MgSO$_4$, filtered and concentrated in vacuo. The product was used crude in the next step.
Yield: 10.9 g.

(f). N-[1-Acetyl-5,7-dimethoxy-4-(4-methoxy-phenyl)-2,2,4-trimethyl-1,2,3,4-tetrahydro-quinolin-6-yl]-3-chloro-2,6-dimethoxy-benzamide General procedure A: To a solution of the compound described in example 1e (100 mg), 3-chloro-2,6-dimethoxy-benzoic acid (60 mg) and DIPEA (132 µl) in CH$_2$Cl$_2$ (2 ml) was added HATU (143 mg) at room temperature. If the reaction did not reach completion after 18 h, more HATU and DIPEA were added. After completion of the reaction a saturated aqueous solution of NaHCO$_3$ was added, the organic layer was separated, dried (MgSO$_4$) and concentrated In vacuo. The title compound was purified by preparative HPLC (method A).
Yield: 87 mg. MS-ESI: [M+H]$^+$=597.4
HPLC: R$_t$=17.98 min (method 1).

Example 2

4,5-Dimethyl-furan-2-carboxylic acid [1-acetyl-5,7-dimethoxy-4-(4-methoxy-phenyl)-2,2,4-trimethyl-1,2,3,4-tetrahydro-quinolin-6-yl]-amide General procedure B: To a solution of the compound described in example 1e (800 mg), 4,5-dimethylfuran-2-carboxylic acid (308 mg) and DMA (768 µl) in DMF (10 ml) was added HATU (1.1 g) at room temperature. If the reaction did not reach completion after 18 h, the reaction mixture was heated to 50° C. After completion of the reaction, water and ethyl acetate were added, the organic layer was separated, dried (MgSO$_4$) and concentrated in vacuo. The title compound was purified by chromatography on silicagel using heptane/ethyl acetate=1/0=>0/1 (v/v) as the eluent.
Yield: 444 mg. MS-ESI: [M+H]$^+$=521.4
HPLC: R$_t$=16.96 min (method 1).

Example 3

5-Bromo-thiophene-2-carboxylic acid [1-acetyl-5,7-dimethoxy-4-(4-methoxy-phenyl)-2,2,4-trimethyl-1,2,3,4-tetrahydro-quinolin-6yl]-amide According to general procedure B, the compound described in example 1e (800 mg), was acylated with 5-bromothiophene-2-carboxylic acid (456 mg), DMA (768 µl) and HATU (1.1 g) in CH$_2$Cl$_2$ (10 ml). The title compound was purified by chromatography on silicagel using heptane/ethyl acetate=1/0=>0/1 (v/v) as the eluent.
Yield: 1.0 g. MS-ESI: [M+H]$^+$=589.2; HPLC: R$_t$=18.90 min (method 2).

Example 4

Biphenyl-4-carboxylic acid [1-acetyl-5,7-dimethoxy-4-(4-methoxy-phenyl)-2,2,4-trimethyl-1,2,3,4-tetrahydro-quinolin-6-yl]-amide General procedure C: To a solution of the compound described in example 1e (800 mg) and 4-biphenylcarbonyl chloride (475 mg) in CH$_2$Cl$_2$ (10 ml) was added DMA (768 µl) at room temperature. The reaction mixture was stirred until no starting material remained at which point water was added. The organic layer was separated, dried (MgSO$_4$) and concentrated in vacuo. The title compound was purified by chromatography on silicagel using heptane/ethyl acetate=1/0=>0/1 (v/v) as the eluent.
Yield: 678 mg. MS-ESI: [M+H]$^+$=579.4; HPLC: R$_t$=26.19 min (method 2).

Example 5

Furan-2-carboxylic acid [1-acetyl-5-hydroxy-7-methoxy-4-(4-methoxy-phenyl)-2,2,4-trimethyl-1,2,3,4-tetrahydro-quinolin-6yl]-amide (a). Furan-2-carboxylic acid [1-acetyl-5,7-dimethoxy-4-(4-methoxyphenyl)-2,2,4-trimethyl-1,2,3,4-tetrahydroquiolin-6-yl]-amide According to general procedure C, the compound described in example 1e (800 mg) was acylated with 2-furoyl chloride (217 µl) and DMA (768 µl) in CH$_2$Cl$_2$ (10 ml). The title compound was purified by chromatography on silicagel using heptane/ethyl acetate=1/0=>0/1 (v/v) as the eluent.
Yield: 896 mg (b). Furan-2-carboxylic acid [1-acetyl-5-hydroxy-7-methoxy-4-(4-methoxy-phenyl)-2,2,4-trimethyl-1,2,3,4-tetrahydro-quinolin-6-yl]-amide General procedure D: A solution of the compound described in example 5a (50 mg) in CH$_2$Cl$_2$ (4 ml) was cooled to −78° C., under an atmosphere of N$_2$. Boron tribromide (28

μl) was added dropwise and after complete addition, the reaction mixture was allowed to slowly warm to room temperature. The reaction was quenched with water and $CH_2Cl_2$ was added. The organic layer was separated, dried ($MgSO_4$) and concentrated in vacuo. The title compound was purified by preparative HPLC (method A). Under the above described conditions, generally mixtures of compounds with a varying degree of demethylation are formed, which may be separated by preparative HPLC methods.

Yield: 9.1 mg; MS-ESI: $[M+H]^+$=479.4; HPLC: $R_t$=23.40 min (method 2).

Example 6

N-[1-Acetyl-5-hydroxy-7-methoxy-4-(4-methoxy-phenyl)-2,2,4-trimethyl-1,2,3,4-tetrahydro-quinolin-6-yl]-3,5-dichloro-benzamide (a). N-[1-Acetyl-5,7-dimethoxy-4-(4-methoxyphenyl)-2,2,4-trimethyl-1,2,3,4-tetra-hydroquinolin-6-yl]-3,5-dichlorobenzamide According to general procedure C, the compound described in example 1e (800 mg) was acylated with 3,5-dichlorobenzoyl chloride (460 mg) and DMA (768 μl) in $CH_2Cl_2$ (10 ml). The title compound was purified by chromatography on silicagel using heptane/ethyl acetate=1/0=>0/1 (v/v) as the eluent.

Yield: 1.03 g (b). N-[1-Acetyl-5-hydroxy-7-methoxy-4-(4-methoxy-phenyl)-2,2,4-trimethyl-1,2,3,4-tetrahydro-quinolin-6-yl]-3,5-dichloro-benzamide According to general procedure D, the compound described in example 6a (50 mg) was treated with boron tribromide (24 μl) in $CH_2Cl_2$ (4 ml). The title compound was is purified by preparative HPLC. (method A).

Yield: 9.6 mg; MS-ESI: $[M+H]^+$=557.2; HPLC: $R_t$=23.40 min (method 2).

Example 7

5-Chloro-thiophene-2-carboxylic acid [1-acetyl-5-hydroxy-7-methoxy-4-(4-methoxy-phenyl)-2,2,4-trimethyl-1,2,3,4-tetrahydro-quinolin-6yl]-amide (a). 5-Chlorothiophene-2-carboxylic acid [1-acetyl-5,7-dimethoxy-4-(4-methoxy-phenyl)-2,2,4-trimethyl-1,2,3,4-tetrahydroquinolin-6-yl]-amide According to general procedure B, the compound described in example 1e (800 mg) was acylated with 5-chlorothiophene-2-carboxylic acid (456 mg), DMA (768 μl) and HATU (1.1 g) in $CH_2Cl_2$ (10 ml). The title compound was purified by chromatography on silicagel using heptane/ethyl acetate=1/0=>0/1 (v/v) as the eluent.

Yield: 1.0 g (b). 5-Chloro-thiophene-2-carboxylic acid [1-acetyl-5-hydroxy-7-methoxy-4-(4-methoxy-phenyl)-2,2,4-trimethyl-1,2,3,4-tetrahydro-quinolin-6-yl]-amide According to general procedure D, the compound described in example 7a (200 mg) was treated with boron tribromide (350 μl) in $CH_2Cl_2$ (25 ml) but in this case the temperature was not allowed to exceed −30° C. The title compound was purified by chromatography on silicagel using heptane/ethyl acetate=1/0=>0/1 (v/v) as the eluent, followed by preparative HPLC (method A).

Yield: 35 mg; MS-ESI: $[M+H]^+$=529.2; HPLC: $R_t$=28.24 min (method 2).

Example 8

Biphenyl-4-carboxylic acid [1-acetyl-5-hydroxy-7-methoxy-4-(4-methoxy-phenyl)-2,2,4-trimethyl-1,2,3,4-tetrahydro-quinolin-6-yl]-amide According to general procedure D, the compound described in example 4 (50 mg) was treated with boron tribromide (100 μl) in $CH_2Cl_2$ (4 ml) but in this case the temperature was not allowed to exceed 0° C. The reaction mixture also contains the product described in example 10. The title compound was purified by chromatography on silicagel using heptane/ethyl acetate=1/0=>0/1 (v/v) as the eluent.

Yield: 43 mg; MS-ESI: $[M+H]^+$=565.4; HPLC: $R_t$=32.53 min (method 2).

Example 9

Biphenyl-4-carboxylic acid [1-acetyl-5,7-dihydroxy-4-(4-hydroxy-phenyl)-2,2,4-trimethyl-1,2,3,4-tetrahydro-quinolin-6-yl]-amide According to general procedure D, the compound described in example 4 (50 mg) was treated with boron tribromide (100 μl) in $CH_2Cl_2$ (4 ml) but in this case the temperature was allowed to reach 15° C. The title compound was purified by chromatography on silicagel using heptane/ethyl acetate=1/0=>0/1 (v/v) as the eluent.

Yield: 33 mg; MS-ESI: $[M+H]^+$=537.4; HPLC: $R_t$=24.16 min (method 2).

Example 10

Biphenyl-4-carboxylic acid [1-acetyl-5-hydroxy-4-(4-hydroxy-phenyl)-7-methoxy-2,2,4-trimethyl-1,2,3,4-tetrahydro-quinolin-6-yl]-amide According to general procedure D, the compound described in example 4 (400 mg) was treated with boron tribromide (800 μl) in $CH_2Cl_2$ (25 ml) but in this case the temperature was not allowed to exceed 0° C. The title compound (=a byproduct as described in example 8) was purified by chromatography on silicagel using heptane/ethyl acetate=1/0=>0/1 (v/v) as the eluent Yield: 50 mg; MS-ESI: $[M+]^+$=551.4; HPLC: $R_t$=27.58 min (method 2).

Example 11

4,5-Dimethyl-furan-2-carboxylic acid [1-acetyl-5-hydroxy-7-methoxy-4-(4-methoxy-phenyl)-2,2,4-trimethyl-1,2,3,4tetrahydro-quinolin-6-yl]-amide According to general procedure D, the compound described in example 2 (200 mg) was treated with boron tribromide (336 μl) in $CH_2Cl_2$ (25 ml) but in this case the temperature was kept at −78° C. The title compound was purified by preparative HPLC method A).

Yield: 51 mg; MS-ESI: $[M+H]^+$=507.4; HPLC: $R_t$=24.32 min (method 1).

Example 12

N-[1-Acetyl-5-hydroxy-4-(4-hydroxy-phenyl)-7-methoxy-2,2,4-trimethyl-1,2,3,4-tetrahydro-quinolin-6-yl]-3,5-dichloro-benzamide According to general procedure D, the compound described in example 6a (75 mg) was treated with boron tribromide (38 µl) in $CH_2Cl_2$ (5 ml. The title compound was purified by preparative HPLC (method A).

Yield: 11 mg; MS-ESI: $[M+R]^+$=543.4; HPLC: $R_t$=25.66 min (method 2).

Example 13

N-[1-Acetyl-5-hydroxy-7-methoxy-4-(4-methoxy-phenyl)-2,2,4-trimethyl-1,2,3,4-tetrahydro-quinolin-6-yl]-3,5-dimethyl-benzamide (a). N-[1-Acetyl-5,7-dimethoxy-4-(4-methoxyphenyl)-2.2,4-trimethyl-1,2,3,4-tetra-hydroquinolin-6-yl]-3,5-dimethyl-benzamide According to general procedure B, the compound described in example 1e (800 mg), was acylated with 3,5-dimethylbenzoic acid (330 mg), DMA (768 µl) and HATU (1.1 g) in $CH_2Cl_2$ (10 ml). The title compound was purified by chromatography on silicagel using heptane/ethyl acetate=1/0=>0/1 (v/v) as the eluent Yield: 1.18 g (b). N-[1-Acetyl-5-hydroxy-7-methoxy-4-(4-methoxy-phenyl)-2,2,4-trimethyl-1,2,3,4-tetrahydro-quinolin-6yl]-3,5-dimethyl-benzamide According to general procedure D, the compound described in example 13a (300 mg) was treated with boron tribromide (513 µl) in $CH_2Cl_2$ (25 ml), but in this case the temperature was not allowed to exceed −40° C. The title compound was purified by preparative HPLC (method A).

Yield: 41 mg, MS-ESI: $[M+H]^+$=517.4; HPLC: $R_t$=13.89 min (method 3).

Example 14

N-[1-Acetyl-5-hydroxy-7-methoxy-4-(4-methoxy-phenyl)-2,2,4-trimethyl-1,2,3,4-tetrahydro-quinolin-6-yl]-3,5-dibromo-benzamide (a). N-[1-Acetyl-5,7-dimethoxy-4-(4-methoxyphenyl)-2,2,4-trimethyl-1,2,3,4-tetra-hydroquinolin-6-yl]-3,5-dibromobenzamide According to general procedure B, the compound described in example 1e (800 mg), was acylated with 3,5-dibromobenzoic acid (616 mg), DMA (768 µl) and HATU (1.1 g) in DMF (10 ml). The title compound was purified by chromatography on silicagel using heptane/ethyl acetate=1/0=>0/1 (v/v) as the eluent Yield: 900 mg (b). N-[1-Acetyl-5-hydroxy-7-methoxy-4-(4-methoxy-phenyl)-2,2,4-trimethyl-1,2,3,4-tetrahydro-quinolin-6-yl]-3,5-dibromo-benzamide According to general procedure D, the compound described in example 14a (300 mg) was treated with boron tribromide (639 µl) in $CH_2Cl_2$ (25 ml), but in this case the temperature was not allowed to exceed −60° C. The title compound was purified by preparative HPLC (method B).

Yield: 28 mg; MS-ESI: $[M+H]^+$=647.2; HPLC: $R_t$=16.29 min (method 3).

Example 15

Biphenyl-4-carboxylic acid [1-acetyl-2,2,4-trimethyl-7-(2-morpholin-4-yl-ethoxy)-4-phenyl-1,2,3,4-tetrahydro-quinolin-6-yl]-amide (a). 1-Fmoc-2-methoxy-4-nitroaniline A solution of 2-methoxy-4-nitroaniline (3.0 g) and pyridine (1.6 ml) in THF (30 ml) was cooled to 0° C. FmocCl (5.07 g) was added in portions and after complete addition the ice-bath was removed and the mixture was stirred for 5 h. The THF was removed in vacuo and the residue dissolved in $CH_2Cl_2$ (175 ml). Methanol (ca 100 ml) was added and the $CH_2Cl_2$ was partly removed in vacuo until a precipitate formed. The mixture was allowed to stand for 1 h, after which time the crystals were collected by filtration and dried in vacuo to give the title compound.

Yield: 6.32 g; MS-ESI: $[M+H]^+$=391.2

(b). 9-Fluorenylmethyl N-(2-methoxy-4-aminophenyl)carbamate

General procedure E: A mixture of the compound described in example 15a (6.07 g), acetic acid (8.9 ml) and THF (150 ml) was cooled to 0° C. Zinc dust (20.4 g) was added in portions and the ice bath was removed. After the temperature slowly reached 10° C. it rapidly rose to 45° C. After the reaction mixture was allowed to cool down to room temperature, the excess of zinc was removed by filtration and a large amount of $CH_2Cl_2$ (Ca 500 ml) was added. The mixture was washed with saturated aqueous $NaHCO_3$ (3×200 ml) and brine (1×200 ml). The organic layer was separated, dried ($MgSO_4$), filtered and concentrated in vacuo until a precipitate formed. The mixture was allowed to stand overnight at 0° C., after which time the crystals were collected by filtration and dried in vacuo to give the title compound.

Yield: 4.45 g.

(c). (7-Methoxy-2,2,4-trimethyl-1,2-dihydroquinolin-6-yl)-carbamic acid 9H-fluoren-9-ylmethyl ester A mixture of the compound described in example 15b (4.45 g), 12 (157 mg), $MgSO_4$ (7.4 g), 4-tert-butylcatechol (61 mg) and acetone (Ca 350 ml) was heated at reflux for 5 h. The $MgSO_4$ was removed by filtration and the filtrate was concentrated in vacuo. The title compound was obtained by chromatography on silicagel using heptane/ethyl acetate=9/1=>7/3 (v/v) as the eluent.

Yield: 4.24 g.

(d). (1-Acetyl-7-methoxy-2,2,4-trimethyl-1,2-dihydroquinolin-6-yl)-carbamic acid 9H-fluoren-9-ylmethyl ester To a solution of the compound described in example 15c (4.24 g) in pyridine (25 ml) and $CH_2Cl_2$ (25 ml) was added a small amount of DMAP (ca 20 mg). Acetyl chloride (2.0 ml) in $CH_2Cl_2$ (20 ml) was slowly added. After complete addition the mixture was diluted with $CH_2Cl_2$ (ca 100 ml) and washed with water (3×100 ml), 0.1 M aq HCl (3×100 ml), 0.5 M aq HCl (1×100 ml) and brine (1×100 ml). The organic layer was dried (MgSO$_4$) and concentrated in vacuo. The title compound was obtained by chromatography on silicagel using heptane/ethyl acetate=9/1=>7/3 (v/v) as the eluent.

Yield: 3.91 g.

e). 1-Acetyl-6-amino-7-methoxy-2,2,4-trimethyl-1,2-dihydroquinoline

Piperidine (8.0 ml) was added to a solution of the compound described in example 15d (3.91 g) in CH$_2$Cl$_2$ (80 ml). After 1.5 h, the reaction mixture was concentrated in vacuo and the title compound was obtained by chromatography on silicagel using heptane/ethyl acetate=9/1>=7/3 (v/v) as the eluent Yield: 2.2 g

(f). Biphenyl-4-carboxylic acid (1-acetyl-7-methoxy-2,2,4-trimethyl-1,2-dihydroquinolin-6yl)-amide General procedure F: To a mixture of the compound described in example 15e (2,2 g), toluene (45 ml) and pyridine (5 ml) was added 4-biphenylcarbonyl chloride (2.21 g). If the reaction did not reach completion after 3 h at room temperature, an additional portion of 4-biphenylcarbonyl chloride (2.0 g) was added. Stirring was continued for 30 min, after which the reaction mixture was concentrated in vacuo. The residue was taken up in ethyl acetate (ca 100 ml) and washed with saturated aq NaHCO$_3$ (100 ml), 1 M aq HCl (3×100 ml) and brine (100 ml). The organic layer was dried (MgSO$_4$) and concentrated in vacuo. To the residue was added CH$_2$Cl$_2$ (ca 50 ml) and the solids were removed by filtration and discarded. The filtrate was concentrated in vacuo and the title compound was obtained by chromatography on silicagel using heptane/ethyl acetate=1/0=>1/1 (v/v) as the eluent.

Yield: 3.1 g.

(g). Biphenyl-4-carboxylic acid (1-acetyl-7-hydroxy-2,2,4-trimethyl-4-phenyl-1,2,3,4-tetrahydroquinolin-6-yl)-amide General procedure G: To a solution of the compound described in example 15f (3.1 g) in benzene (100 ml) was added aluminum trichloride (5.6 g) and the reaction mixture was stirred for 20 h at room temperature. The reaction was quenched with H$_2$O (ca 100 ml) and the pH of the mixture was adjusted to pH 8 with 2 M aq NaOH while stirring vigorously. Ethyl acetate (ca 300 ml) was added and the organic layer was washed with H$_2$O (2×150 ml) and brine (1×150 ml), dried (MgSO$_4$) and concentrated in vacuo to yield the product that was used without further purification.

Yield: 3.5 g.

(h). Biphenyl-4-carboxylic acid [1-acetyl-2,2,4-trimethyl-7-(2-morpholin-4-yl-ethoxy)-4-phenyl-1,2,3,4-tetrahydro-quinolin-6-yl]-amide General procedure H: A mixture of the compound described in example 15g (70 mg), N-(2-chloroethyl)-morpholine hydrochloride (31 mg), Cs$_2$CO$_3$ and DMF (3 ml) was stirred at 50° C., until no starting material remained. The reaction mixture was diluted with ethyl acetate (15 ml) and water was added (ca 15 ml). The organic layer was washed with water (3×15 ml), separated, dried (MgSO$_4$), filtered and concentrated in vacuo. The title compound was obtained as the corresponding HCl salt by lyophilization from a mixture of 1,4-dioxane and H$_2$O containing HCl.

Yield: 63 mg (HCl salt); MS-ESI: [M+H]$^+$=618.6; HPLC: R$_t$=19.49 min (method 4).

Example 16

Biphenyl-4-carboxylic acid (1-acetyl-7-dimethylcarbamoylmethoxy-2,2,4-trimethyl-4-phenyl-1,2,3,4-tetrahydro-quinolin-6-yl)-amide According to general procedure H, the compound described in example 15g (79 mg) was alkylated with 2-chloro-N,N-methylacetamide (23 mg) and Cs$_2$CO$_3$ (255 mg) in DMF (2 ml). The title compound was purified by crystallization from CH$_3$CN.

Yield: 15 mg; MS-ESI: [M+H]$^+$=590.6; HPLC: R$_t$=23.58 min (method 5).

Example 17

Biphenyl-4-carboxylic acid [1-acetyl-2,2,4trimethyl-4-phenyl-7-(3-piperidin-1-yl-propoxy)-1,2,3,4-tetrahydro-quinolin-6-yl]-amide According to general procedure H, the compound described in example 15g (79 mg) was alkylated with N-(3-chloropropyl)piperidine hydrochloride (37.4 mg) and Cs$_2$CO$_3$ (255 mg) in DMF (2 ml). The title compound was purified by crystallization from CH$_3$CN.

Yield: 83 mg (HCl salt); MS-ESI: [M+]$^+$=630.8; HPLC: R$_t$=15.49 min (method 5).

Example 18

Biphenyl-4-carboxylic acid [1-acetyl-2,2,4-trimethyl-4-phenyl-7-(pyridin-2-ylmethoxy-1,2,3,4-tetrahydro-quinolin-6-yl]-amide According to general procedure H, the compound described in example 15g (79 mg) was alkylated with 2-picolyl chloride hydrochloride (31 mg) and Cs$_2$CO$_3$ (255 mg) in DMF (2 ml). The title compound was purified by crystallization from CH$_3$CN.

Yield: 32 mg (HCl salt); MS-ESI: [M+H]$^+$=596.6; HPLC: R$_t$=22.41 min (method 6).

Example 19

Biphenyl-4-carboxylic acid [1-acetyl-2,2,4-trimethyl-4-phenyl-7-(pyridin-3-ylmethoxy)-1,2,3,4-tetrahydro-quinolin-6-yl]-amide According to general procedure H, the compound described in example 15g (79 mg) was alkylated with 3-picolyl chloride hydrochloride (31 mg) and Cs$_2$CO$_3$ (255 mg) in DMF (2 ml). The title compound was purified by crystallization from CH$_3$CN.

Yield: 36 mg (HCl salt); MS-ESI: [M+H]$^+$=596.6; HPLC: R$_t$=19.70 min (method 6).

Example 20

Biphenyl4-carboxylic acid [1-acetyl-2,2,2trimethyl-4-phenyl-7-(pyridin-4-ylmethoxy)-1,2,3,4-tetrahydro-quinolin-6-yl]-amide According to general procedure H, the compound described in example 15g (79 mg) was alkylated with 4-picolyl chloride hydrochloride (31 mg) and Cs$_2$CO$_3$ (255 mg) in DMF (2 ml). The title compound was purified by crystallization from CH$_3$CN Yield: 31 mg (HCl salt); MS-ESI: [M+H]$^+$=596.4; HPLC: R$_t$=17.09 min (method 6).

Example 21

Biphenyl-4-carboxylic acid [1-acetyl-7-(2-dimethylamino-ethoxy)-2,2,4-trimethyl-4-phenyl-1,2,3,4-tetrahydro-quinolin-6-yl]-amide According to general procedure H, the compound described in example 15g (79 mg) was alkylated with 2-dimethylaminoethylchloride hydrochloride (27 mg) and Cs$_2$CO$_3$ (255 mg) in DMF (2 ml). The title compound was purified by crystallization from CH$_3$CN.

Yield: 55 mg (HCl salt); MS-ESI: [M+H]$^+$=576.6; HPLC: R$_t$=14.94 min (method 5).

Example 22

Biphenyl-4-carboxylic acid (1-acetyl-7-carbamoyl-methoxy-2,2,4-trimethyl-4-phenyl-1,2,3,4-tetrahydro-quinolin-yl)-amide According to general procedure H, the compound described in example 15g (79 mg) was alkylated with 2-chloroacetamide (18 mg) and Cs$_2$CO$_3$ (255 mg) in DMF (2 ml). The title compound was purified by preparative HPLC (method A).

Yield: 60.2 mg; MS-ESI: [M+H]$^+$=562.4; HPLC: R$_t$=20.47 min (method 5).

Example 23

Morpholine-4-carboxylic acid (3-{1-acetyl-6-[(biphenyl-4-carbonyl)-amino]-2,2,4-trimethyl-4-phenyl-1,2,3,4-tetrahydro-quinolin-7-yloxy}-propyl)-amide According to general procedure H, the compound described in example 15g (79 mg) was alkylated with morpholine-4-carboxylic acid (3-chloropropyl)amide (40 mg) and Cs$_2$CO$_3$ (255 mg) in DMF (2 ml). The title compound was purified by preparative HPLC (method A).

Yield: 52.4 mg; MS-ESI: [M+H]$^+$=675.6; HPLC: R$_t$=22.31 min (method 5).

Example 24

Furan-2-carboxylic acid 1-acetyl-6-(3,5-dibromo-benzoylamino)-2,2,4-trimethyl-4-phenyl-1,2,3,4-tetrahydro-quinolin-7-yl ester (a). N-(1-Acetyl-7-methoxy-2,2,4-trimethyl-1,2-dihydroquinolin-6-yl)-3,5-dibromo-benzamide According to general procedure F, the compound described in example 15e (1.0 g) was acylated with 3,5-dibromobenzoyl chloride (1.72 g) in toluene (9 ml) and pyridine (1 ml). The title compound was obtained by chromatography on silicagel using heptane/ethyl acetate=8/2 (v/v) as the eluent.

Yield: 1.3 g (b). N-(1-Acetyl-7-hydroxy-2,2,3-trimethyl-4-phenyl-1,2,3,4-tetrahydroquinolin-6-yl)-3,5-dibromo-benzamide According to general procedure G, the compound described in example 24a (1.3 g) was stirred with AlCl$_3$ (1.0 g) in benzene (50 ml). The product obtained was used without further purification.

Yield: 1.39 g (c). Furan-2-carboxylic acid 1-acetyl-6-(3,5-dibromo-benzoylamino)-2,2,4-trimethyl-4-phenyl-1,2,3,4-tetrahydro-quinolin-7-yl ester A mixture of the compound described in example 24b (100 mg), furoyl chloride (16 µl) and DIPEA (60 µl) and CH$_2$Cl$_2$ (5 ml) was stirred at room temperature until no starting material remained. Water was added and the organic layer was separated, washed with brine, dried (MgSO$_4$) and concentrated in vacuo. The title compound was purified by preparative HPLC (method A).

Yield: 47 mg, MS-ESI: [M+H]$^+$=681.2; HPLC: R$_t$=31.6 min (method 2).

Example 25

N-[1-Acetyl-7-(2-amino-ethoxy)-2,2,4-trimethyl-4-phenyl-1,2,3,4-tetrahydro-quinolin-6-yl]-3,5-dibromo-benzamide General procedure I: A mixture of the compound described in example 24b (100 mg), tert-butyl N-(2-hydroxyethyl)carbamate (29 mg), DtBAD (79 mg), DIPEA (60 µl) and an excess of polymer bound triphenylphosphine in CH$_2$Cl$_2$ (5 ml) was stirred at room temperature until no starting material remained. The reaction mixture was filtered and washed with water and brine. The organic layer was separated, dried (MgSO$_4$) and concentrated in vacuo. The crude product was taken up in CH$_3$CN (ca 1 ml) and a few drops of TFA were added facilitating cleavage of the tert-butylcarbamate. The title compound was purified by preparative HPLC (method A).

Yield: 17 mg (TFA salt); MS-ESI: [M+H]$^+$=630.2; HPLC: R$_t$=15.6 min (method 2).

Example 26

{2-[1-Acetyl-6-(3,5-dimethyl-benzoylamino)-2,2,4-trimethyl-4-phenyl-1,2,3,4-tetrahydro-quinolin-7-yloxy]-ethyl}-carbamic acid tert-butyl ester (a). N-(1-Acetyl-7-methoxy-2,2,4trimethyl-1,2-dihydroquinolin-6yl)-3,5-dimethyl-benzamide According to general procedure F, the compound described in example 15e (1.0 g) was acylated with 3,5-dimethylbenzoyl chloride (0.97 g) in toluene (9 ml) and pyridine (1 ml). The title compound was obtained by chromatography on silicagel using heptane/ethyl acetate=8/2 (v/v) as the eluent.

Yield: 1.1 g (b). N-(1-Acetyl-7-hydroxy-2,2,4-trimethyl-4-phenyl-1,2,3,4-tetrahydroquinolin-6-yl)-3,5-dimethyl-benzamide According to general procedure G, the compound described in example 26a (1.1 g) was stirred with AlCl$_3$ (1.0 g) in benzene (50 ml). The product obtained was used without further purification.

Yield: 1.3 g (c). {2-[1-Acetyl-6-(3,5-dimethyl-benzoylamino)-2,
2,4-trimethyl-4-phenyl-1,2,3,4-tetrahydro-quinolin-
7-yloxy]-ethyl}-carbamic acid tert-butyl ester According to general procedure I, the compound described in example 26b (100 mg) was alkylated with tert-butyl N-(2-hydroxyethyl)carbamate (37 mg), DtBAD (101 mg), DIPEA (77 μl) and an excess of polymer bound triphenylphosphine in CH$_2$Cl$_2$ (5 ml). In this case the tert-butylcarbamate was not cleaved, affording the title product after preparative HPLC (method A) and lyophilization.

Yield: 38 mg; MS-ESI: [M+H]$^+$=600.4; HPLC: R$_t$=33.1 min (method 2).

Example 27

N-[1-Acetyl-7-(furan-2-ylmethoxy)-2,2,4-trimethyl-
4-phenyl-1,2,3,4-tetrahydro-quinolin-6yl]-3,5-dim-
ethyl-benzamide According to general procedure I, the compound described in example 26b (100 mg) was alkylated with 2-(hydroxymethyl)furan (21 μl), DtBAD (101 mg), DIPEA (77 μl) and an excess of polymer bound triphenylphosphine in CH$_2$Cl$_2$ (5 ml). The title product was purified by preparative HPLC (method A), followed by lyophilization.

Yield: 16 mg, MS-ESI: [M+H]$^+$=537.4; HPLC: R$_t$=32.8 min (method 2).

Example 28

N-[1-Acetyl-2,2,4-trimethyl-4- phenyl-7-(pyridin-4-
ylmethoxy)-1,2,3,4-tetrahydro-quinolin-6-yl]-3,5-
dichloro-benzamide (a). N-(1-Acetyl-7-methoxy-2,2,4-trimethyl-1,2-
dihydroquinolin-6-yl)-3,5-dichloro-benzamide According to general procedure F, the compound described in example 15e (1.0 g) was acylated with 3,5-dichlorobenzoyl chloride (12 g) in toluene (9 ml) and pyridine (1 ml). The title compound was obtained by chromatography on silicagel using heptane/ethyl acetate=8/2 (v/v) as the eluent.

Yield: 1.47 g (b). N-(1-Acetyl-7-hydroxy-2,2,4-trimethyl-4-phe-
nyl-1,2,3,4-tetrahydroquinolin-6-yl)-3,5-dichlo-
robenzamide According to general procedure G, the compound described in example 28a (1.47 g) was stirred with AlCl$_3$ (1.5 g) in benzene (75 ml). The product obtained was used without further purification.

Yield: 1.51 g (c). N-[1-Acetyl-2,2,4-trimethyl-4-phenyl-7-(pyri-
din-4-ylmethoxy)-1,2,3,4-tetrahydro-quinolin-6-yl]-
3,5-dichloro-benzamide According to general procedure H, the compound described in example 28b (100 mg) was alkylated with 4-picolyl chloride hydrochloride (36 mg) and Cs$_2$CO$_3$ (255 mg) in a mixture of DMF (1 ml) and CH$_2$Cl$_2$ (4 ml). The title compound was obtained as the corresponding TFA salt after preparative HPLC (method A), followed by lyophilization.

Yield: 35 mg (TFA salt); MS-ESI: [M+H]$^+$=588.4; HPLC: R$_t$=18.0 min (method 2).

Example 29

N-[1-Acetyl-2,2,4-trimethyl-4-phenyl-7-(2-pyrroli-
din-1-yl-ethoxy)-1,2,3,4-tetrahydro-quinolin-6-yl]-3,
5-dimethyl-benzamide General procedure J: A mixture of the compound described in example 26b (100 mg), 2-chloroethylpyrrolidine hydrochloride (41 mg) and DIPEA (77 μl) in CH$_2$Cl$_2$ (5 ml) was stirred at room temperature until no more starting material remained. Water was added and the organic layer was separated, washed with brine, dried (NgSO$_4$) and concentrated in vacuo. Purification by means of preparative HPLC, followed by lyophilization gave the title compound as the corresponding TFA salt.

Yield: 104 mg (TFA salt); MS-ESI: [M+H]$^+$=554.4; HPLC: R$_t$=15.2 min (method 2).

Example 30

N-[1-Acety--2,2,4-trimethyl-7-(5-methyl-isoxazol-3-
ylmethoxy)-4-phenyl-1,2,3,4-tetrahydro-quinolin-6-
yl]-3,5-dimethyl-benzamide According to general procedure J, the compound described in example 26b (100 mg) was alkylated with (chloromethyl)-5-methylisooxazole (32 mg) and DIPEA (77 μl) in CH$_2$Cl$_2$ (5 ml). Purification by means of preparative HPLC (method A), followed by lyophilization gave the title compound.

Yield: 41 mg, MS-ESI: [M+H]$^+$=552,4; HPLC: R$_t$=31.3 min (method 2).

Example 31

N-[1-Acetyl-7-(2-diethylamino-ethoxy)-2,2,4-trim-
ethyl-4-phenyl-1,2,3,4-tetrahydro-quinolin-6-yl]-3,5-
diethyl-benzamide: compound with trifluoro-acetic
acid According to general procedure J, the compound described in example 26b (100 mg) was alkylated with N,N-diethylaminoethylchloride hydrochloride (42 mg) and DIPEA (77 μl) in CH$_2$Cl$_2$ (5 ml). Purification by means of preparative HPLC (method A), followed by lyophilization gave the tide compound as its corresponding TFA salt.

Yield: 43 mg (TFA salt); MS-ESI: [M+H]$^+$=556.4; HPLC: R$_t$=15.2 min (method 2).

Example 32

N-[1-Acetyl-2,2,4-trimethyl-4-phenyl-7-(pyridin-4-
ylmethoxy)-1,2,3,4-tetrahydro-quinolin-yl]-5-
bromo-2-methylamino-benzamide (a). N-(1-Acetyl-7-methoxy-2,2,4-trimethyl-1,2-
dihydroquinolin-6-yl)-5-bromo-2-methylamino-ben-
zamide According to general procedure F, the compound described in example 15e (1.0 g) was acylated with 5-bromo-2-methylamino-benzoyl chloride (1.43 g) in toluene (9 ml) and pyridine (1 ml). The title compound was obtained by chromatography on silicagel using heptane/ethyl acetate=8/2 (v/v) as the eluent.

Yield: 595 mg

(b). N-(1-Acetyl-7-hydroxy-2,2,4-trimethyl-4-phenyl-1,2,3,4-tetrahydroquinolin-6-yl)-5-bromo-2-methylamino-benzamide According to general procedure G, the compound described in example 32a (595 mg) was stirred with AlCl$_3$ (0.75 g) in benzene (50 ml). The product obtained was used without further purification.

Yield: 437 mg

(c). N-[1-Acetyl-2,2,4-trimethyl-4-phenyl-7-(pyridin-4-ylmethoxy)-1,2,3,4-tetrahydro-quinolin-6-yl]-5-bromo-2-methylamino-benzamide According to general procedure H, the compound described in example 32b (44 mg) was alkylated with 4-picolyl chloride hydrochloride (15 mg) and Cs$_2$CO$_3$ (ca 100 mg) in a mixture of DMF (1 ml) and CH$_2$Cl$_2$ (4 ml). The tile compound was obtained as the corresponding TFA salt after preparative HPLC (method B).

Yield: 18 mg (TFA salt); MS-ESI: [M+H]$^+$=629.4; HPLC: R$_t$=18.1 min (method 2).

Example 33

Furan-2-carboxylic acid (1-acetyl-7-dimethylamino-2,2,4-trimethyl-4-phenyl-1,2,3,4-tetrahydro-quinolin-6-yl)-amide

(a). (2,2,4-Trimethyl-1,2-dihydroquinolin-6-yl)carbamic acid tert-butyl ester A mixture of N-Boc-1,4-phenylenediamine (75 g), MgSO$_4$ (216 g), 4-tert-butylcatechol (1.8 g) and iodine (4.7 g) in anhydrous acetone (600 ml) was refluxed for 20 h. The MgSO$_4$ was removed by filtration and the filtrate was concentrated in vacuo. The residue was chromatographed on a short plug of silicagel using heptane/ethyl acetate=8/2 (v/v) as the eluent to give the product as a brown oil.

Yield: 41 g.

(b). (1-Acetyl-2,2,4-trimethyl-1,2-dihydroquinolin-6-yl)-carbamic acid tert-butyl ester A solution of the compound described in example 33a (41 g) in pyridine (200 ml) and CH$_2$Cl$_2$ (200 ml) was cooled to 0° C. Acetyl chloride (21 ml) in CH$_2$Cl$_2$ (50 ml) was added dropwise. After complete addition the mixture was stirred for 3 h at room temperature. Ethyl acetate (2 l) and H$_2$O (2 l) were added and the organic layer was separated, dried (MgSO$_4$) and concentrated in vacuo. The title compound was obtained by crystallization from ethyl acetate.

Yield: 23 g.

(c). 1-Acetyl-6-amino-2,2,4-trimethyl-4-phenyl-1,2,3,4-tetrahydroquinoline

According to general procedure G, the compound described in example 33b (33.3 g) was stirred with AlCl$_3$ (40.4 g) in benzene (700 ml). The product was purified by chromatography on silicagel using heptane/ethyl acetate=8/2 (v/v) as the eluent.

Yield: 22.4 g

(d). (1-Acetyl-2,2,4-trimethyl-4-phenyl-1,2,3,4-tetrahydroquinolin-6-yl)-carbamic acid 9-fluorenylmethyl ester Pyridine (6.4 ml) was added to a solution of the compound described in example 33c (22,4 g) in THF (300 ml) and the resulting mixture was cooled to 0° C. A solution of FmocCl (20.7 g) in THF (100 ml) was added dropwise and after the addition was complete the mixture was stirred for 1 h at room temperature. The reaction mixture was concentrated in vacuo and ethyl acetate (800 ml) and 0.3 M aq HCl (500 ml) were added. The organic layer was separated and washed with 0.3 M HCl (2×500 ml), H$_2$O (500 ml) and brine (500 ml), followed by drying (MgSO$_4$) and concentration in vacuo. The product was used without further purification in the next step.

Yield: 43 g

(e) (1-Acetyl-2,2,4-trimethyl-7-nitro-4-phenyl-1,2,3,4-tetrahydroquinolin-6-yl)-carbamic acid 9-fluorenylmethyl ester Fuming nitric acid (3.07 ml) was added dropwise over a period of 10 min to a mixture of the compound described in example 33d (43 g) and acetic acid (230 ml) in CH$_2$Cl$_2$ (230 ml). The reaction mixture was stirred until full conversion of starting material after which H$_2$O (150 ml) was added. The aqueous layer was separated and extracted with CH$_2$Cl$_2$ (150 ml). The combined organic layers were washed with saturated aq NaHCO$_3$ (3×200 ml) and brine (200 ml), followed by drying over MgSO$_4$ and filtration. Methanol (ca 200 ml) was added and the CH$_2$Cl$_2$ was carefully removed in vacuo, after which the mixture was allowed to stand at room temperature overnight. The bright yellow crystals were collected by filtration and dried (MgSO$_4$) in vacuo.

Yield: 29.3 g.

(f). (1-Acetyl-7-amino-2,2,4-trimethyl-4-phenyl-1,2,3,4-tetrahydroquinolin-6-yl)-carbamic acid 9-fluorenylmethyl ester According to general procedure E, the compound described in example 33e (20 g) was reduced using zinc dust (45 g) and acetic acid (20 ml) in THF (ca 600 ml), to give the product which was used crude in the next step.

Yield: 21 g

(g) (1-Acetyl-7-dimethylamino-2,2,4-trimethyl-4-phenyl-1,2,3,4-tetrahydroquinolin-6-yl)-carbamic acid 9-fluorenylmethyl ester An aqueous solution of formaldehyde (37%, 3.8 ml) was added to a solution of the compound described in example 33f (12 g), acetic acid (15.7 ml) and sodium cyanoborohydride (2.9 g) in methanol (200 ml), which gave rise to an exothermic reaction and the formation of a white precipitate. An additional amount of MeOH was added to facilitate stirring. After stirring for 15 min, the precipitate was collected by filtration and washed with MeOH/H$_2$O=1/1 (v/v). The filtrate was partly concentrated to give more solid material which was also collected. The combined solids were recrystallized from CH$_2$Cl$_2$/MeOH to give the dimethylated compound.

Yield: 9.7 g

(h). 1-Acetyl-6-Amino-7-dimethylamino-2,2,4-trimethyl-4-phenyl-1,2,3,4-tetrahydro-quinoline Piperidine (7.7 ml) was added to a solution of the compound described in example 33g (4.5 g) in $CH_2Cl_2$ (70 ml). After 24 h, the reaction mixture was diluted with $CH_2Cl_2$ (100 ml) and washed with 0.5 M aq HCl (2×150 ml), water (100 ml) and brine (1 ml). The organic layer was dried ($MgSO_4$) and diluted to a total volume of 200 ml. This stock solution of the title compound (ca 13.8 mg/ml) was used for further reactions.

(i). Furan-2-carboxylic acid (1-acetyl-7-dimethylamino-2,2,4-trimethyl-4-phenyl-1,2,3,4-tetrahydroquinolin-6-yl)-amide Triethylamine (38 µl) and 2-furoyl chloride (27 µl) were added to a solution of the compound described in example 33h (96.6 mg) in $CH_2Cl_2$ (10 ml) and the resulting mixture was stirred until full conversion of starting material was achieved. The title compound was purified by chromatography on silicagel using heptane/ethyl acetate=1/0=>0/1 (v/v) as the eluent.

Yield: 5.5 mg. MS-ESI: $[M+H]^+$=4462; HPLC: $R_t$=19.02 min (method 2).

Example 34

5-Methyl-thiophene-2-carboxylic acid (1-acetyl-7-dimethylamino-2,2,4-trimethyl-4-phenyl-1,2,3,4-tetrahydro-quinolin-6-yl)-amide According to general procedure A, the compound described in example 33h (96.6 mg) was acylated with 5-methylthiophene-2-carboxylic acid (39.1 mg), HATU (157 mg) and DIPEA (239 µl) in $CH_2Cl_2$ (10 ml). The title compound was purified by preparative HPLC (method B).

Yield: 35.5 mg; MS-ESI: $[M+H]^+$=476.2; HPLC: $R_t$=21.26 min (method 2).

Example 35

Biphenyl-4-carboxylic acid (1-acetyl-7-dimethylamino-2,2,4-trimethyl-4-phenyl-1,2,3,4-tetrahydroquinolin-6-yl)-amide According to general procedure A, the compound described in example 33h (96.6 mg) was acylated with 4-biphenylcarboxylic acid (54.4 mg), HATU (157 mg) and DIPEA (239 µl) in $CH_2Cl_2$ (10 ml). The title compound was purified by preparative HPLC (method B).

Yield: 31.5 mg; MS-ESI: $[M+H]^+$=532.4; HPLC: $R_t$=24.92 min (method 2).

Example 36

N-(1-Acetyl--7dimethylamino-2,2,4-trimethyl-4-phenyl-1,2,3,4-tetrahydro-quinolin-6-yl)-3,5-dibromo-benzamide According to general procedure A, the compound described in example 33h (96.6 mg) was acylated with 3,5-dibromobenzoic acid (77 mg), HATU (157 mg) and DIPEA (239 µl) in $CH_2Cl_2$ (10 ml). The title compound was purified by crystallization from $CH_2Cl_2/CH_3CN$.

Yield: 24.3 mg, MS-ESI: $[M+H]^+$=614.2; HPLC: $R_t$=27.71 min (method 2).

Example 37

Cyclopentanecarboxylic acid (1-acetyl-7-dimethylamino-2,2,4-trimethyl-4-phenyl-1,2,3,4-tetrahydroquinolin-6yl)-amide According to general procedure A, the compound described in example 33h (137 mg) was acylated with cyclopentanecarboxylic acid (128 µl), HATU (224 mg) and DIPEA (400 µl) in $CH_2Cl_2$ (10 ml). The title compound was purified by chromatography on silicagel using heptane/ethyl acetate=1/0=>0/1 (v/v) as the eluent.

Yield: 148 mg; MS-ESI: $[M+H]^+$=448.4; HPLC: $R_t$=12.93 min (method 1).

Example 38

N-(1-Acetyl-7-dimethylamino-2,2,4-trimethyl-4-phenyl-1,2,3,4-tetrahydro-quinolin-6-yl)-isobutyramide According to general procedure A, the compound described in example 33h (137 mg) was acylated with isobutyric acid (110 µl), HATU (224 mg) and DIPEA (400 µl) in $CH_2Cl_2$ (10 ml). The title compound was purified by chromatography on silicagel using heptane/ethyl acetate=1/0=>0/1 (v/v) as the eluent.

Yield: 43 mg, MS-ESI: $[M+H]^+$=422.4; HPLC: $R_t$=9.99 min (method 1).

Example 39

Furan-2-carboxylic acid (1-acetyl-7-furan-2-ylcarbonylamino-2,2,4-trimethyl-4-phenyl-1,2,3,4-tetrahydroquinolin-6-yl)-amide To solution of the compound described in example 33f (150 mg) and triethylamine (43 µl) in $CH_2Cl_2$ (1 ml) was added 2-furoyl chloride (30 µl). After complete consumption of starting material, 1 M aqueous HCl was added, the organic layer was separated followed by the addition of piperidine (1 ml) and the resulting mixture was stirred overnight The reaction mixture was washed with 1 M aqueous HCl, the organic layer separated, dried ($MgSO_4$) and concentrated in vacuo. The title compound was purified by chromatography on silicagel using heptane/ethyl acetate=1/0=>0/1 (v/v) as the eluent, followed by preparative HPLC (method A).

Yield: 18 mg; MS-ESI: $[M+H]^+$=512.4; HPLC: $R_t$=19.92 min (method 2).

Example 40

5-Methyl-thiophene-2-carboxylic acid (1-acetyl-2,2,4-trimethyl-4-phenyl-7-propylamino-1,2,3,4-tetrahydro-quinolin-6-yl)-amide

(a). 1-Acetyl-6-amino-2,2,4-trimethyl-4-phenyl-7-propylamino-1,2,3,4-tetrahydroquinoline General procedure K: To a mixture of the compound described in example 33f (750 mg), acetic acid (953 µl), sodium cyanoborohydride (135 mg) and MeOH (10 ml) was added propionaldehyde (94.2 µl). The mixture was sired for 18 h, water was added and the precipitate was collected by filtration. The precipitate was taken up in $CH_2Cl_2$ (10 ml), piperidine (1 ml) was added and the resulting mixture was stirred for 18 h. The reaction mixture was washed with 1 M aqueous HCl, the organic layer was separated and diluted to a total volume of 50 ml. This solution was used for following reactions.

(b). 5-Methyl-thiophene-2-carboxylic acid (1-acetyl-2,2,4-trimethyl-4-phenyl-7-[(pyridin-4 ylmethyl)-amino]-1,2,3,4-tetrahydro-quinolin-6-yl)-amide According to general procedure A, the compound described in example 40a (100 mg) was acylated with 5-methylthiophene-2-carboxylic acid (39.1 mg), HATU (157 mg) and DIPEA (239 µl) in $CH_2Cl_2$ (10 ml). The title compound was purified by preparative HPLC and lyophilized.

Yield: 18.3 mg; MS-ESI: $[M+H]^+$=490.4; HPLC: $R_t$=23.96 min (method 2).

Example 41

Biphenyl-4-carboxylic acid (1-acetyl-7-ethylamino-2,2,4-trimethyl-4-phenyl-1,2,3,4-tetrahydro-quinolin-6-yl)amide (a). 1-Acetyl-6-amino-7-ethylamino-2,2,4-trimethyl-4-phenyl-1,2,3,4-tetrahydroquinoline According to general procedure K, the compound described in example 33f (750 mg) was alkylated using acetaldehyde (73.3 µl), and deprotected with piperidine (1 ml) to give after work up and dilution a solution of the title compound in $CH_2Cl_2$.

(b). Biphenyl-4-carboxylic acid (1-acetyl-7-ethylamino-2,2,4-trimethyl-4-phenyl-1,2,3,4-tetrahydro-quinolin-6-yl)-amide According to general procedure A, the compound described in example 41a (100 mg) was acylated with 4-biphenylcarboxylic acid (54.4 mg), HATU (157 mg) and DIPEA (239 µl) in $CH_2Cl_2$ (10 ml). The title compound was purified by preparative HPLC and lyophilized.

Yield: 9.8 mg, MS-ESI: $[M+H]^+$=532.4; HPLC: $R_t$=25.55 min (method 2).

Example 42

5-Methyl-thiophene-2-carboxylic acid {1-acetyl-2,2,4-trimethyl-4-phenyl-7-[(pyridin-4-ylmethyl)-amino]-1,2,3,4-tetrahydro-quinolin-6-yl}-amide (a). 1-Acetyl-6-amino-2,2,4-trimethyl-4-phenyl-7-[(pyridin-4-ylmethyl)-amino]-1,2,3,4-tetrahydro-quinoline According to general procedure K, the compound described in example 33f (750 mg) was alkylated using 4-pyridinecarboxaldehyde (125 µl), and deprotected with piperidine (1 ml) to give after work up and dilution a solution of the title compound in $CH_2Cl_2$.

(b). 5-Methyl-thiophene-2carboxylic acid {1-acetyl-2,2,4-trimethyl-4-phenyl-7-[(pyridin-4-ylmethyl)-amino]-1,2,3,4-tetrahydro-quinolin-6-yl}-amide According to general procedure A, the compound described in example 42a (114 mg) was acylated with 5-methylthiophene-2-carboxylic acid (39.1 mg), HATU (157 mg) and DIPEA (239 µl) in $CH_2Cl_2$ (10 ml). The title compound was purified by preparative HPLC and lyophilized.

Yield: 51 mg; MS-ESI: $[M+H]^+$=539.4; HPLC: $R_t$=13.19 min (method 2).

Example 43

5-Methyl-thiophene-2-carboxylic acid {1-acetyl-2,2,4-trimethyl-4-phenyl-7-[(pyridin-3-ylmethyl)-amino-]1,2,3,4-tetrahydro-quinolin-6-yl}-amide (a). 1-Acetyl-6-amino-2,2,4-trimethyl-4-phenyl-7-[(pyridin-3-ylmethyl)-amino]-1,2,3,4-tetrahydro-quinoline According to general procedure K, the compound described in example 33f (750 mg) was alkylated using 3-pyridinecarboxaldehyde (125 µl), and deprotected with piperidine (1 ml) to give after work up and dilution a solution of the title compound in $CH_2Cl_2$.

(b). 5-Methyl-thiophene-2-carboxylic acid {1-acetyl-2,2,4-trimethyl-4-phenyl-7-[(pyridin-3-ylmethyl)-amino]-1,2,3,4-tetrahydro-quinolin-6-yl}-amide According to general procedure A, the compound described in example 43a (114 mg) was acylated with 5-methylthiophene-2-carboxylic acid (39.1 mg), HATU (157 mg) and DIPEA (239 µl) in $CH_2Cl_2$ (10 ml). The title compound was purified by preparative HPLC and lyophilized.

Yield: 44 mg; MS-ESI: $[M+H]^+$=539.4; HPLC: $R_t$=13.45 min (method 2).

Example 44

N-(1-Acetyl-7-isobutylamino-2,2,4-trimethyl-4-phenyl-1,2,3,4-tetrahydro-quinolin-6-yl)-3,5-dibromo-benzamide (a). 1-Acetyl-6-amino-7-isobutylamino-2,2,4-trimethyl-4-phenyl-1,2,3,4-tetrahydroquinoline According to general procedure K, the compound described in example 33f (750 mg) was alkylated isobutyraldehyde (119 µl), and deprotected with piperidine (1 ml) to give after work up and dilution a solution of the title compound in $CH_2Cl_2$.

(b). N-(1-Acetyl-7-isobutylamino-2,2,4-trimethyl-4-phenyl-1,2,3,4-tetrahydro-quinolin-6-yl)-3,5-dibromo-benzamide According to general procedure A, the compound described in example 44a (114 mg) was acylated with 3,5-dibromobenzoic acid (77 mg), HATU (157 mg) and DIPEA (239 µl) in $CH_2Cl_2$ (10 ml). The title compound was purified by preparative HPLC and lyophilized.

Yield: 54 mg; MS-ESI: $[M+H]^+$=642.4; HPLC: $R_t$=29.47 min (method 2).

Example 45

Biphenyl-4-carboxylic acid (1-acetyl-7-benzylamino-2,2,4-trimethyl-4-phenyl-1,2,3,4-tetrahydroquinolin-6-yl)-amide (a). 1-Acetyl-6-amino-7-benzylamino-2,2,4-trimethyl-4-phenyl-1,2,3,4-tetrahydroquinoline According to general procedure K, the compound described in example 33f (750 mg) was alkylated using benzaldehyde (133 µl), and deprotected with piperidine (1 ml) to give after work up and dilution a solution of the title compound in $CH_2Cl_2$.

(b). Biphenyl-4-carboxylic acid (1-acetyl-7-benzylamino-2,2,4-trimethyl-4-phenyl-1,2,3,4-tetrahydroquinolin-6-yl)-amide According to general procedure A, the compound described in example 45a (113 mg) was acylated with 4-biphenylcarboxylic acid (54.4 mg), HATU (157 mg) and DIPEA (239 µl) in $CH_2Cl_2$ (10 ml). The title compound was purified by preparative HPLC and is lyophilized.
Yield: 114 mg; MS-ESI: $[M+H]^+=594.4$; HPLC: $R_t=26.46$ min (method 2).

Example 46

5-Methyl-thiophene-2-carboxylic acid (1-acetyl-7-benzylamino-2,2,4-trimethyl-4-phenyl-1,2,3,4-tetrahydro-quinolin-6-yl)-amide According to general procedure A, the compound described in example 45a (113 mg) was acylated with 5-methylthiophene-2-carboxylic acid (39.1 mg), HATU (157 mg) and DIPEA (239 µl) in $CH_2Cl_2$ (10 ml). The title compound was purified by preparative HPLC and lyophilized.
Yield: 107 mg, MS-ESI: $[M+H]^+=538.4$; HPLC: $R_t=18.59$ min (method 2).

Example 47

N-{1-Acetyl-2,2,4-trimethyl-4-phenyl-7-[pyridin-3-ylmethyl)-amino-]1,2,3,4-tetrahydro-quinolin-6-yl}-3,5-dibromo-benzamide According to general procedure A, the compound described in example 43a (114 mg) was acylated with 3,5-dibromobenzoic acid (77 mg), HATU (157 mg) and DIPEA (239 µl) in $CH_2Cl_2$ (10 ml). The title compound was purified by preparative HPLC and lyophilized.
Yield: 41 mg, MS-ESI: $[M+H]^+=677.2$; HPLC: $R_t=14.88$ min (method 2).

Example 48

N-(1-Acetyl-7-dimethylamino-4-methyl-4-phenyl-1,2,3,4-tetrahydro-quinolin-6-yl)-3,5-dibromo-benzamide (a). 4-Methyl-1,2-dihydroquinoline A solution of lepidine (10.0 g) in THF was cooled down to −78° C., after which a solution of $BH_3$.THF in THF (1 M, 70 ml) was added. After 2 h, a solution of sodium bis(2-methoxyethoxy)aluminum dihydride in toluene (3.5 M, 40 ml) was added and the reaction mixture was stirred for an additional 2 h. Water was added and the mixture diluted with ethyl acetate. The organic layer was separated, dried ($MgSO_4$) and partially concentrated in vacuo causing crystallization of the title compound. The crystals were collected by filtration to yield 3.5 g after drying in vacuo. The remaining mother liquor was concentrated in vacuo and the residue was purified by chromatography on silicagel using heptane/ethyl acetate=0/1=>1/0 ( (v/v) as the eluent to give an additional 4.4 g of the title compound.
Yield: 7.9 g.

(b). 1-Acetyl-4-methyl-1,2-dihydroquinoline

According to general procedure C, the compound described in example 48a (7.9 g) was acylated with acetyl chloride (11.8 ml) and DMA (34 ml) in $CH_2Cl_2$ (50 ml) at 0° C. The title compound was purified by chromatography on silicagel using heptane/ethyl acetate=6/4 as the eluent.
Yield: 8.8 g (c). 1-Acetyl-4-methyl-4-phenyl-1,2,3,4-tetrahydroquinoline According to general procedure G, the compound described in example 48b (8.8 g) was stirred with $AlCl_3$ (18.8 g) in benzene (250 ml). The product obtained was used without further purification.
Yield: 12.0 g (d). 1-Acetyl-4methyl-6-nitro-4-phenyl-1,2,3,4-tetrahydroquinoline To a solution of the compound described in example 48c (5.0 g) and acetic anhydride (189 µl) in $CH_2Cl_2$ (50 ml) was added dropwise fuming $HNO_3$ (9.4 ml). After the reaction was complete, water was added and the organic layer was washed with brine, separated and concentrated in vacuo. The title compound was purified by chromatography on silicagel using heptane/ethyl acetate=6/4 (v/v) as the eluent
Yield: 3.86 g (e). 1-Acetyl-6-amino-4-methyl-4-phenyl-1,2,3,4-tetrahydroquinoline According to general procedure E, the compound described in example 48d (3.86 g) was reduced using zinc dust (16 g) and acetic acid (7 ml) in THF (ca 250 ml), to give the product which was used crude in the next step.
Yield: 2.2 g (f). (1-Acetyl-4-methyl-4-phenyl-1,2,3,4-tetrahydroquinolin-6-yl)-carbamic acid 9-fluorenylmethyl ester Pyridine (314 µl) was added to a solution of the compound described in example 48e (1.0 g) in THF (10 ml) and the resulting mixture was cooled to 0° C. FmocCl (1.01 g) was added and the mixture was stirred for 18 h at room temperature, after which time the reaction mixture was concentrated in vacuo. The title compound was purified by chromatography on silicagel using heptane/ethyl acetate=6/4 (v/v) as the eluent
Yield: 950 mg

(g). (1-Acetyl-4-methyl-7-nitro-4-phenyl-1,2,3,4-tetrahydroquinolin-6-yl)-carbamic acid 9-fluorenylmethyl ester To a solution of the compound described in example 48f (850 mg) and acetic anhydride (17 μl) in CH$_2$Cl$_2$ (5 ml) was added dropwise fuming HNO$_3$ (842 μl). After the reaction was complete, water was added and the organic layer was washed with brine, separated and concentrated in vacuo. The title compound was purified by chromatography on silicagel using heptane/ethyl acetate=9/1=>0/1 (v/v) as the eluent.
Yield: 714 mg

(h). (1-Acetyl-7-amino-4-methyl-4-phenyl-1,2,3,4-tetrahydroquinolin-6-yl)-carbamic acid 9-fluorenylmethyl ester According to general procedure B, the compound described in example 48g (2.37 g) was reduced using zinc dust (5.6 g) and acetic acid (2.4 ml) in THF (ca 50 ml), to give the product which was used crude in the next step.
Yield: 2.66 g

(i). (1-Acetyl-7-dimethylamino-4-methyl-4-phenyl-1,2,3,4-tetrahydroquinolin-6-yl)-carbamic acid 9-fluorenylmethyl ester An aqueous solution of formaldehyde (37%, 650 μl) was added to a solution of the compound described in example 48h (2.66 g), acetic acid (3.1 ml) and sodium cyanoborohydride (232 mg) in methanol (50 ml), and the resulting mixture was stirred for 18 h. The reaction mixture was concentrated in vacuo and the residue was taken up in ethyl acetate and washed with water and brine. The organic layer was separated, dried (MgSO$_4$) and concentrated in vacuo. The title compound was purified by chromatography on silicagel using heptane/ethyl acetate=9/1=>0/1 (v/v) as the eluent.
Yield: 1.0 g

(j). 1-Acetyl-6-amino-7-dimethylamino-4-methyl-4-phenyl-1,2,3,4-tetrahydroquinoline Piperidine (1.8 ml) was added to a solution of the compound described in example 48i (1 g) in CH$_2$Cl$_2$ (20 ml) and the mixture was stirred until no more starting material remained. The reaction mixture was concentrated in vacuo, and the title compound was purified by chromatography on silicagel using heptane/ethyl acetate=9/1=>0/1 (v/v) as the eluent.
Yield: 370 mg.

(k). N-(1-Acetyl-7-dimethylamino-4-methyl-4-phenyl-1,2,3,4-tetrahydro-quinolin-6-yl)-3,5-dibromobenzamide According to general procedure A, the compound described in example 48j (74 mg) was acylated with 3,5-dibromobenzoic acid (70 mg), HATU (131 mg) and DIPEA (120 μl) in CH$_2$Cl$_2$ (3 ml). The title compound was purified by preparative HPLC and lyophilized.
Yield: 82 mg; MS-ESI: [M+H]$^+$=586.2; HPLC: R$_t$=22.40 min (method 2).

Example 49

5-Bromo-thiophene-2-carboxylic acid (1-acetyl-7-dimethylamino-4-methyl-4-phenyl-1,2,3,4-tetrahydro-quinolin-6-yl)-amide According to general procedure A, the compound described in example 48j (74 mg) was acylated 5-bromothiophene-2-carboxylic acid (52 mg), HATU (131 mg) and DIPEA (120 μl) in CH$_2$Cl$_2$ (3 ml). The title compound was purified by preparative HPLC and lyophilized.
Yield: 69 mg; MS-ESI: [+H]$^+$=514.2; HPLC: R$_t$=17.01 min (method 2).

Example 50

5-Chloro-thiophene-2-carboxylic acid (1-acetyl-7-dimethylamino-4-methyl-4-phenyl-1,2,3,4-tetrahydro-quinolin-6-yl)-amide According to general procedure A, the compound described in example 48j (74 mg) was acylated 5-chlorothiophene-2-carboxylic acid (52 mg), HATU (131 mg) and DIPEA (120 μl) in CH$_2$Cl$_2$ (3 ml). The title compound was purified by preparative HPLC and lyophilized.
Yield: 81 mg; MS-ESI: [M+H]$^+$=468.2; HPLC: R$_t$=17.49 min (method 2).

Example 51

CHO-FSH in Vitro Bioactivity

FSH activity of compounds were tested in Chinese Hamster Ovary (CHO) cells stably transfected with the human FSH receptor and cotransfected with a cAMP responsive element (CRE)/promotor directing the expression of a firefly luciferase reporter gene. Binding of ligand to the Gs-coupled FSH receptor will result in an increase of cAMP, which in turn will induce an increased transactivation of the luciferase reporter construct. To test antagonistic properties recombinant FSH in a concentration that induces approximately 80% of the maximal stimulation of cAMP accumulation in the absence of test compound was added (rec-hFSH, 10 mU/ml). The luciferase signal was quantified using a luminescence counter. For test compounds, EC$_{50}$ values (concentration of test compound causing half-maximal (50%) stimulation or reduction) were calculated For that purpose the software program GraphPad PRISM, version 3.0 (GraphPad software Inc., San Diego) was used.

Compounds of all examples exhibited an EC$_{50}$ (IC$_{50}$) value of less than 10$^{-5}$ M in either an agonistic or antagonistic assay set-up or both. The compounds of examples 5-8, 10-14, 16, 18-20, 33-35, 37, 38, 41 and 45-50 showed an EC$_{50}$ of less than 10$^{-7}$ M in at least one of the assays.

The invention claimed is:
1. A tetrahydroquinoline derivative according to Formula 1,

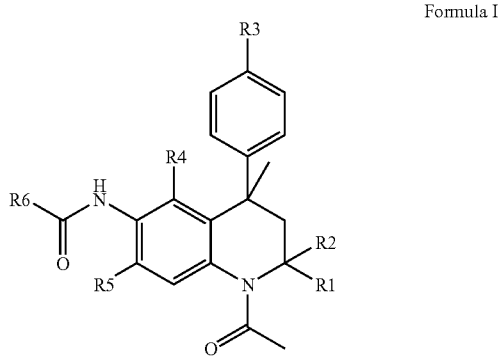

Formula I or a pharmaceutically acceptable salt thereof, wherein
R$^1$ and R$^2$ are H or Me
R$^3$ is H, hydroxy, (1-4C)alkoxy, $R^4$ is H, OH, or (1-4C)alkoxy, $R^5$ is OH, (1-4C)alkoxy or $R^7$, with the proviso that if $R^4$ is H, $R^5$ is not OH or (1-4C)alkoxy $R^6$ is (2-5C)heteroaryl, (6C)aryl, (3-8C)cycloalkyl, or (1-6C)alkyl, wherein the (2-5C)heteroaryl and the (6C)aryl are optionally substituted with one or more substituents selected from hydroxyl, amino, halogen, phenyl, (1-4C)alkyl, (1-4C)alkoxy, or (1-4C)(di)alkylamino, $R^7$ is amino, (di)(1-4C)alkylamino, (2-5C)heteroarylcarbonylamino, (2-5C)heteroarylcarbonyloxy, $R^8$-(2-4C)alkoxy, $R^9$-methylamino or $R^9$-methoxy $R^8$ is amino, (di)(1-4C)alkylamino, (2-6C)heterocycloalkyl, (2-6C)heterocycloalkylcarbonylamino, or (1-4C)alkoxycarbonylamino and $R^9$ is aminocarbonyl, (di)(1-4C)alkylaminocarbonyl, (2-5C)heteroaryl, optionally substituted with one or more (1-4C)alkyl substituents, or (6C)aryl.

2. The tetrahydroquinoline derivative of claim 1 wherein $R^8$ is amino, (di)(1-4C)alkylamino, (2-6C)heterocycloalkyl or (2-6C)heterocycloalkylcarbonylamino.

3. The tetrahydroquinoline derivative of claim 1 wherein $R^7$ is (di)(1-4C)alkylamino, $R^8$-(2-4C)alkoxy, $R^9$-methylamino or $R^9$-methoxy.

4. The tetrahydroquinoline derivative of claim 3 wherein $R^8$ is amino, (di)(1-4C)alkylamino or (2-6C)heterocycloalkyl.

5. The tetrahydroquinoline derivative of claim 4 wherein $R^8$ is (di)(1-4C)alkylamino or (2-6C)heterocycloalkyl.

6. The tetrahydroquinoline derivative of claim 3 wherein $R^6$ is (2-5C)heteroaryl or (6C)aryl.

7. The tetrahydroquinoline derivative of claim 1 wherein $R^6$ is (4-5C)heteroaryl or (6C)aryl and R9 is aminocarbonyl, (di)(1-4C)alkylaminocarbonyl, (3-5C)heteroaryl or (6C)aryl.

8. The tetrahydroquinoline derivative of claim 1 wherein $R^7$ is (di)(1-4C)alkylamino, $R^8$-ethoxy, $R^9$-methylamino or $R^9$-methoxy and $R^9$ is aminocarbonyl, (di)(1-4C)alkylaminocarbonyl, (3-5C)heteroaryl or (6C)aryl.

9. The tetrahydroquinoline derivative of claim 1 wherein $R^8$ is (di)(1-4C)alkylamino or (4-5C)heterocycloalkyl and $R^9$ is aminocarbonyl, (di)(1-4C)alkylaminocarbonyl, (3-5C)heteroaryl or (6C)aryl.

10. A pharmaceutical composition comprising the tetrahydroquinoline derivative of claim 1 and at least one pharmaceutically suitable auxiliary.

* * * * *